(12) United States Patent

Tarze et al.

(10) Patent No.: US 9,402,821 B2
(45) Date of Patent: Aug. 2, 2016

(54) METHODS AND PHARMACEUTICAL COMPOSITIONS FOR TREATMENT OF CYSTIC FIBROSIS

(71) Applicants: INSERM (Institut National de la sante et de la Recherche Medicale), Paris (FR); Universite Paris-Est Creteil Val de Marne, Creteil Cedex (FR); Assistance Publique-Hopitaux de Paris, Paris (FR)

(72) Inventors: Agathe Tarze, Creteil Cedex (FR); Pascale Fanen, Creteil Cedex (FR)

(73) Assignees: INSERM (Institut National de la Sante et de la Recherche Medicale), Paris (FR); Universite Paris-Est Creteil Val de Marne, Creteil (FR); Assistance Publique-Hopitaux de Paris, Paris (FR)

( * ) Notice: Subject to any disclaimer, the term of this patent is extended or adjusted under 35 U.S.C. 154(b) by 0 days.

(21) Appl. No.: 14/421,541

(22) PCT Filed: Aug. 13, 2013

(86) PCT No.: PCT/EP2013/066859
§ 371 (c)(1),
(2) Date: Feb. 13, 2015

(87) PCT Pub. No.: WO2014/026959
PCT Pub. Date: Feb. 20, 2014

(65) Prior Publication Data
US 2015/0182480 A1  Jul. 2, 2015

(30) Foreign Application Priority Data

Aug. 13, 2012  (EP) .................................... 12305999

(51) Int. Cl.
*A01N 37/10* (2006.01)
*A61K 31/19* (2006.01)
*A61K 31/192* (2006.01)
*A61K 45/06* (2006.01)

(52) U.S. Cl.
CPC ............... *A61K 31/192* (2013.01); *A61K 45/06* (2013.01)

(58) Field of Classification Search
None
See application file for complete search history.

(56) References Cited

U.S. PATENT DOCUMENTS

| 2004/0077612 | A1* | 4/2004 | Mercep | C07J 43/003 514/175 |
| 2007/0021357 | A1* | 1/2007 | Tobia | A61K 31/4152 514/23 |
| 2008/0319026 | A1* | 12/2008 | Gant | C07D 213/64 514/345 |
| 2009/0192195 | A1 | 7/2009 | Armer | |
| 2013/0186801 | A1* | 7/2013 | Verwijs | A61K 9/28 206/570 |

FOREIGN PATENT DOCUMENTS

| GB | 2457040 A | 8/2009 |
| WO | 2005041864 A2 | 5/2005 |
| WO | 2009105234 A2 | 8/2009 |
| WO | 2009137400 A2 | 11/2009 |
| WO | 2011088474 A2 | 7/2011 |

OTHER PUBLICATIONS

Prasher, "Ibuprofen and Sulindac Decrease T84 and PD Cell Proliferation and Affect Expression of the CFTR Promoter in Transfected PD Cells In Vitro", Retrieved From the Internet: https://cache.kzoo.edu/handle/10920/23123?show=full, 1996.
Imanifooladi et al., "The Role of Nuclear Factor-[kappa]B in Inflammatory Lung Disease", Inflammation and Allergy, 2010, vol. 9, No. 3, p. 197-205.

* cited by examiner

*Primary Examiner* — Jared D Barsky
(74) *Attorney, Agent, or Firm* — Whitham, Curtis & Cook, P.C.

(57) ABSTRACT

The present invention relates to a method and compositions for the treatment of cystic fibrosis.

2 Claims, 13 Drawing Sheets

METHODS AND PHARMACEUTICAL COMPOSITIONS FOR TREATMENT OF CYSTIC FIBROSIS

FIELD OF THE INVENTION

Figure 1:
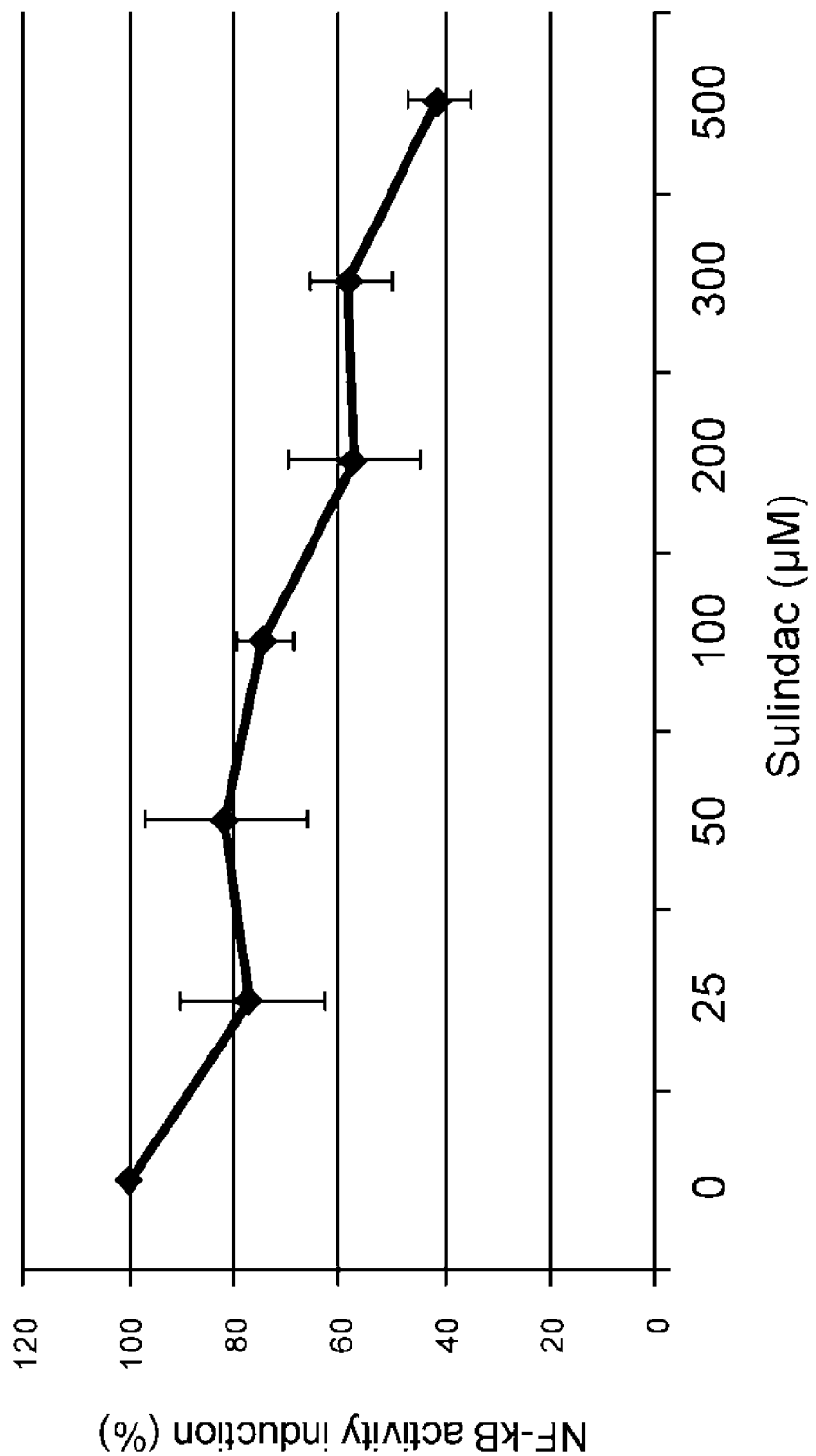
Figure 1:
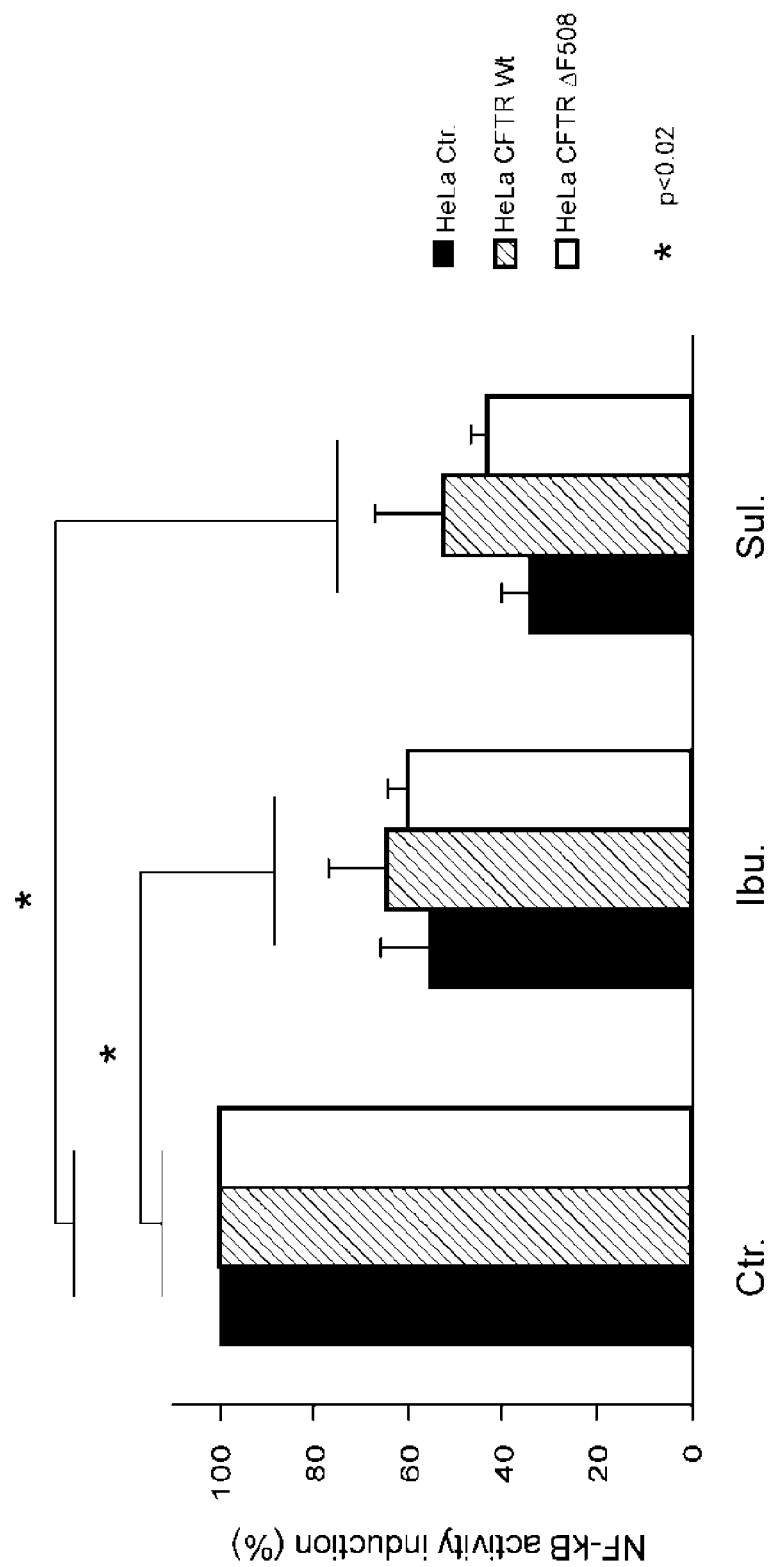

The present invention relates to a method and compositions for the treatment of cystic fibrosis.

BACKGROUND OF THE INVENTION

Pulmonary manifestations are largely responsible for morbidity and mortality in cystic fibrosis (CF). This genetic disease is characterized by progressive lung damage due to chronic infection and exaggerated airway inflammation. Cystic fibrosis bronchial epithelial cells produce high levels of proinflammatory mediators, including interleukin 8 (IL-8), which causes the intense recruitment of neutrophils. The persistent influx of neutrophils into the airway is responsible of lung injury. The synthesis of several proinflammatory mediators is enhanced by hyper activation of intracellular transcription factor nuclear factor kappa B (NF-κB) in cystic fibrosis [1]. Currently, the only therapy recommended by Cystic Fibrosis Foundation (CFF) to lessen the excessive inflammatory response in the airways is a high dose of ibuprofen, a non-steroidal anti-inflammatory drug (NSAID). Two independent clinical trials showed significant preservation of Forced Expiratory Volume (FEV1) and other beneficial clinical effects of ibuprofen [2-4]. Unfortunately, adverse effects or concerns thereof have limited its clinical use. Mechanisms independent of cyclooxygenases inhibition have been proposed to explain the high dose ibuprofen effects and a recent study showed that ibuprofen inhibits the transcriptional activity of NF-κB in CF cells [5]. However, this inhibition is not accompanied by a decreased of IL-8 production. Therefore, it is crucial to develop new and safer anti-inflammatory medications and identify other molecules more effective at the IL-8 level in the context of cystic fibrosis.

Sulindac is used for the short and long term treatment of rheumatoid arthritis, ankylosing spondylitis, gouty arthritis, and osteoarthritis. It is a prodrogue that is metabolized by redox reaction in sulindac sulfide and sulindac sulfone derivatives. In cells, sulindac sulfide is generated by reduction by methionine sulfoxide reductase and inhibits cyclooxygenase activity. Oxidation of sulindac produces sulindac sulfone, a derivate that does not inhibit cyclooxygenase. A new feature of sulindac has been reported with the detection of anti-carcinogenic effects. The precise mechanisms by which sulindac compounds induce apoptosis are not known but seem independent of the inhibition of prostaglandin production. Indeed, sulindac sulfone, like sulindac sulfide, inhibits growth and induces apoptosis in a variety of human tumour cell lines [6,7], COX-2(%) fibroblasts [8] or human prostate cancer cells in nude mouse xenograft model [9]. Recent studies suggest that it may involve an increased production of ceramide, inhibition of the peroxisome proliferator-activated receptors, and/or inhibition of the NF-κB pathway [10]. All these targets are consistent in the context of cystic fibrosis.

SUMMARY OF THE INVENTION

The present invention relates to sulindac or sulindac derivatives for use in the treatment of cystic fibrosis in a subject in need thereof.

DETAILED DESCRIPTION OF THE INVENTION

The role of sulindac in cystic fibrosis was investigated by inventors using bronchial epithelial cells, HeLa cells transfected with wild-type and deltaF508-CFTR, mouse model of lung inflammation, and human primary nasal epithelial cells. The inventors found that sulindac inhibits transcriptional activity of NF-κB. The inventors also demonstrated that sulindac decreases IL-8 transcription and secretion in bronchial epithelial cells and in HeLa cells. The inventors also demonstrated that pretreatment by sulindac decreases keratinocyte-derived chemokine and MIP-2 in the mouse model of inflammation. The Inventors have also investigated the effect of sulindac on various factors disrupted in cystic fibrosis and demonstrated that sulindac has a beneficial effect and causes a decrease in transcriptional activity of AP-1 induced by TNFα in HeLa cells and induce an increase in the transcriptional activity of PPARγ in HeLa cells. The inventors have also demonstrated that the effects of sulindac on NF-κB and IL-8 are independent on that anti-COX activity; therefore the therapeutic effects of sulindac are not in relation to the major target of NSAIDs. In addition to anti-inflammatory effect of sulindac in cystic fibrosis, the inventors surprisingly demonstrated that sulindac induces a significant increase of the mature form of CFTR associated with an increase of chloride channel activity. Therefore, the use of sulindac constitutes a new pharmacological approach to overcome inflammation in cystic fibrosis and inflammatory pulmonary disease. In addition, sulindac constitutes a new pharmacological approach to overcome the causes of cystic fibrosis.

Therapeutic Methods and Uses

Accordingly the present invention relates to sulindac or sulindac derivatives for use in the treatment of cystic fibrosis in a subject in need thereof.

As used herein, the term "subject" denotes a mammal. In a preferred embodiment of the invention, a subject according to the invention refers to any subject (preferably human) afflicted or at risk to be afflicted with cystic fibrosis or inflammatory pulmonary disease.

The method of the invention may be performed for any type of cystic fibrosis such as revised in the World Health Organisation Classification of cystic fibrosis and selected from the E84 group: mucoviscidosis, Cystic fibrosis with pulmonary manifestations, Cystic fibrosis with intestinal manifestations and Cystic fibrosis with other manifestations.

The method of the invention may also be performed for any type of inflammatory pulmonary disease such as revised in the World Health Organisation Classification of inflammatory pulmonary disease and selected from the J32 group: Chronic sinusitis, J33 group: Nasal polyp, the J40-47 group: Chronic lower respiratory diseases, bronchitis, simple and mucopurulent chronic bronchitis, emphysema, chronic obstructive pulmonary disease, asthma, status asthmaticus, bronchiectasis and the J68 group: Respiratory conditions due to inhalation of chemicals, gases, fumes and vapours.

As used herein, the term "sulindac" has its general meaning in the art and refers to (Z)-5-fluoro-2-methyl-1-[p-(methylsulfinyl)benzylidene]-indene-3-acetic acid (Duggan, 1981) having the following formula (I):

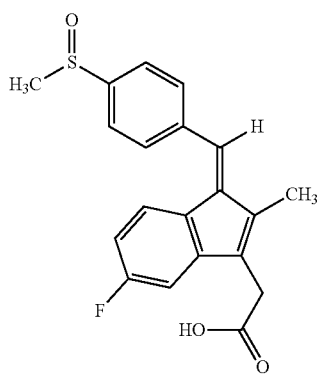

(I)

The term "sulindac" also refers to sulindac sulfide having the following formula (II):

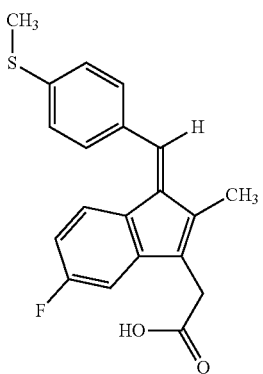

(II)

or sulindac sulfone having the following formula (III):

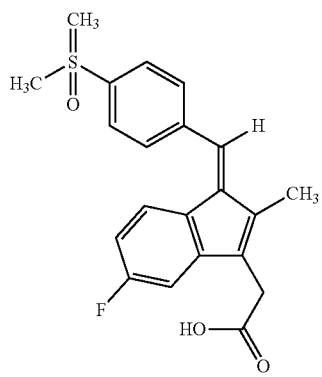

(III)

The terms "sulindac derivatives" has its general meaning in the art and refers to compounds described in U.S. Pat. No. 3,654,349, WO2011/088474, WO2009/023631, WO2011/130486, Cheng et al., 2013 and Zhou et al., 2010 having the general formula (IV):

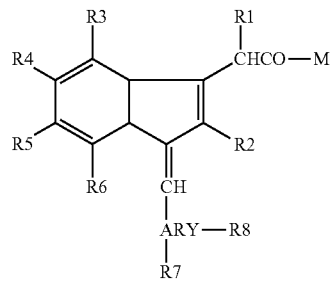

(IV)

Wherein:
ARY is aryl or heteroaryl;
R1 is hydrogen, loweralkyl or halogenated loweralkyl;
R2 is hydrogen or alkyl;
R3, R4, R5 and R6 each are hydrogen, alkyl, acyloxy, alkoxy, nitro, amino, acylamino, alkylamino, dialkylamino, dialkylaminoalkyl, sulfamyl, alkythio, mercapto, hydroxy, hydroxyalkyl, alkylsulfonyl, halogen, cyano, carboxyl, carbalkoxy, carbamido, halogenoalkyl, cycloalkyl or cycloalkoxy;
R7 is alkylsulfinyl or alkylsulfonyl;
R8 is hydrogen, halogen, hydroxy, alkoxy, alkyl, haloalkyl, or thioalkyl; and
M is hydroxy, loweralkoxy, substituted loweralkoxy, amino, alkylamino, dialkylamino, N-morpholino, hydroxyalkylamino, polyhydroxyalkylamino, dialkylaminoalkylamino, aminoalkylamino, and the group OMe, in which Me is a cation.

The indene nucleus may be substituted in the 1-position by an aryl ring system such as benzene, naphthalene or biphenyl or a heteroaryl ring system such as a pyrrole, furan, thiophene, pyridine, imidazole, pyrazine, thiazole, etc. which contains an alkylsulfinyl or alkylsulfonyl substituent and may be further substituted with a halogen (chloro, fluoro or bromo), hydroxy, alkoxy (methoxy, ethoxy, propoxy, etc.) or haloalkyl (fluoromethyl, chloromethyl, trifluoromethyl, etc.) group.

In the most preferred compounds of this invention R3, R4, R5 and R6 each may be halogen (fluoro, chloro or bromo), loweralkoxy (methoxy, ethoxy, i-propoxy, etc.), loweralkyl (methyl, ethyl, propyl, isopropyl, etc.), nitro, amino or substituted amino such as dialkylamino, acylamino, alkylamino, etc. R3, R4, R5 and R6 are not however limited to this class and may, if desired, represent substituents such as hydrogen, aryl, aryloxy, hydroxy, mercapto, haloalkyl, sulfamyl, carboxy, carboalkoxy, carbamido and many other groups.

The term "aryl" as used herein is a ring radical containing 6 to 18 carbons, or preferably 6 to 12 carbons, comprising at least one aromatic residue therein.

Examples of such aryl radicals include phenyl, naphthyl, and isochroman radicals. Moreover, the term "aryl" as used throughout the specification and claims is intended to include both "unsubstituted aryls" and "substituted aryls", the later denotes an aryl ring radical as defined above that is substituted with one or more, preferably 1, 2, or 3 organic or inorganic substituent groups, which include but are not limited to a halogen, alkyl, alkenyl, alkynyl, hydroxyl, cycloalkyl, amino, mono-substituted amino, di-substituted amino, unsubstituted or substituted amido, carbonyl, halogen, sulfhydryl, sulfonyl, sulfonate, sulfamoyl, sulfonamide, azido acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy or haloalkoxy, aryl, substituted aryl, heteroaryl, heterocyclic ring, ring wherein the terms are defined herein. The organic substituent groups can comprise from 1 to 12 carbon atoms, or from 1 to 6 carbon atoms, or from 1 to 4 carbon atoms. It will be understood by those skilled in the art that the moieties substituted on the "aryl" may themselves be substituted, as described above, if appropriate.

The term "heteroaryl" as used herein refers to an aryl ring radical as defined above, wherein at least one of the aryl ring carbons has been replaced with a heteroatom, which include but are not limited to nitrogen, oxygen, and sulfur atoms. Examples of heteroaryl residues include pyridyl, bipyridyl, furanyl, and thiofuranyl residues. Substituted "heteroaryl" residues may have one or more organic or inorganic substituent groups, as referred to hereabove for aryl groups, bound to the carbon atoms of the heteroaromatic rings. The organic substituent groups may comprise from 1 to 12 carbon atoms, or from 1 to 6 carbon atoms, or from 1 to 4 carbon atoms.

The term "hydrogen" as used herein with a respect to a substituent on an organic moiety has it usual and ordinary meaning.

The term "alkyl" as used herein is a branched or unbranched saturated hydrocarbon moiety. "Unbranched" or "Branched" alkyls comprise a non-cyclic, saturated, straight or branched chain hydrocarbon moiety having from 1 to 24 carbons, 1 to 12 carbons, 1 to 6 carbons, or 1 to 4 carbon atoms. Examples of such alkyl radicals include methyl, ethyl, propyl, butyl, pentyl, hexyl, heptyl, octyl, n-propyl, iso-propyl, butyl, n-butyl, sec-butyl, t-butyl, amyl, t-amyl, n-pentyl and the like.

Moreover, the term "alkyl" as used throughout the specification and claims is intended to include both "unsubstituted alkyls" and "substituted alkyls", the latter denotes an alkyl radical analogous to the above definition that is further substituted with one, two, or more additional organic or inorganic substituent groups. Suitable substituent groups include but are not limited to H, alkyl, alkenyl, alkynyl, hydroxyl, cycloalkyl, heterocyclyl, amino, mono-substituted amino, di-substituted amino, unsubstituted or substituted amido, carbonyl, halogen, sulfhydryl, sulfonyl, sulfonate, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl.

It will be understood by those skilled in the art that an "alkoxy" may be a substitutent of a carbonyl substituted "alkyl" forming an ester. When more than one substituent group is present then they can be the same or different. The organic substituent moieties may comprise from 1 to 12 carbon atoms, or from 1 to 6 carbon atoms, or from 1 to 4 carbon atoms. It will be understood by those skilled in the art that the moieties substituted on the "alkyl" chain may themselves be substituted, as described above, if appropriate.

The term lower "lower alkyl" as used herein refers to a $C_{1-4}$ alkyl group, and includes both substituted and substituted lower alkyls.

The term "cycloalkyl" as used herein refers to a hydrocarbon structure wherein the structure is closed to form at least one ring. Cycloalkyls typically comprise a cyclic radical containing 3 to 8 ring carbons, such as cyclopropyl, cyclobutyl, cyclopentyl, cyclopenyl, cyclohexyl, cycloheptyl and the like. Cycloalkyl radicals can be multicyclic and can contain a total of 3 to 18 carbons, or preferably 4 to 12 carbons, or 5 to 8 carbons. Examples of multicyclic cycloalkyls include decahydronapthyl, adamantyl, and like radicals.

Moreover, the term "cycloalkyl" as used throughout the specification and claims is intended to include both "unsubstituted cycloalkyls" and "substituted cycloalkyls", the later denotes an cycloalkyl radical analogous to the above definition that is further substituted with one, two, or more additional organic or inorganic substituent groups that may include but are not limited to hydroxyl, cycloalkyl, amino, mono-substituted amino, di-substituted amino, unsubstituted or substituted amido, carbonyl, halogen, sulfhydryl, sulfonyl, sulfonate, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl. When the cycloalkyl is substituted with more than one substituent group, they may be the same or different. The organic substituent groups may comprise from 1 to 12 carbon atoms, or from 1 to 6 carbon atoms, or from 1 to 4 carbon atoms.

The term "cycloalkenyl" as used herein refers to a cycloalkyl radical as defined above that comprises at least one carbon-carbon double bond. Examples include but are not limited to cyclopropenyl, 1-cyclobutenyl, 2-cyclobutenyl, 1-cyclopentenyl, 2-cyclopeiitenyl, 3-cyclopentenyl, 1-cyclohexyl, 2-cyclohexyl, 3-cyclohexyl and the like.

The term "alkenyl" as used herein refers to an alkyl residue as defined above that also comprises at least one carbon-carbon double bond. Examples include but are not limited to vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2-heptenyl, 3-heptenyl, 4-heptenyl, 5-heptenyl, 6-heptenyl and the like. The term "alkenyl" includes dienes and trienes of straight and branch chains.

The term "alkynyl" as used herein refers to an alkyl residue as defined above that further comprises at least one carbon-carbon triple bond. Examples include but are not limited ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "alkoxy" as used herein refers to an alkyl residue, as defined above, bonded directly to an oxygen atom, which is then bonded to another moiety. Examples include methoxy, ethoxy, n-propoxy, iso-propoxy, n-butoxy, t-butoxy, iso-butoxy and the like.

The term "substituted" as used herein with respect to lower alkoxy groups refers to an —OR group, in which R is an alkyl group that bears at least one substituent.

The term "cycloalkoxy" as used herein refers to an alkoxy group in which the alkyl portion is cycloalkyl.

The term "haloalkoxy" as used herein refers to a haloalkyl residue as defined above that is directly attached to an oxygen to form trifluoromethoxy, pentafluoroethoxy, 2-chloroethoxy, or the like.

As used herein, the terms "halo-," "halogen," "halogenated" and similar terms refer to a fluoro, chloro, bromo or iodo group.

The term "haloalkyl" as used herein refers to an alkyl residue as defined above, that is substituted with one or more halogens, such as a trifluoromethyl, pentafluoroethyl, chloromethyl and the like.

The term "acyl" as used herein refers to a R—C(O)— residue having an organic R group containing 1 to 8 carbons. Examples include but are not limited to formyl, acetyl, propionyl, butanoyl, iso-butanoyl, pentanoyl, hexanoyl, heptanoyl, benzoyl and the like, and natural or un-natural amino acids.

The term "acyloxy" as used herein refers to an acyl radical as defined above, directly attached to an oxygen to form an organic R—C(O)O— residue. Examples include but are not limited to acetyloxy, propionyloxy, butanoyloxy, iso-butanoyloxy, benzoyloxy and the like.

The term "nitro" as used herein refers to a —N⁺(=O)—O— group.

As used herein, the term "azide", "azido" and their variants refer to any moiety or compound comprising the monovalent group —$N_3$ or the monovalent ion $N_3^-$.

The term "hydroxy" and "hydroxyl" as used herein refer to an —OH group.

The term "hydroxyalkyl" as used herein refers to an alkyl substituent that is substituted with a hydroxyl group.

The term "cyano" as used herein refers to a —C≡N group.

The term "amino" as used herein without modification refers to a —NH—, group.

The terms "alkylamine" and "alkylamino" as used herein refer to a moiety comprising an NH radical substituted with one organic substituent group, which includes but is not limited to alkyls, substituted alkyls, cycloalkyls, aryls, or arylalkyls. Examples of alkylamino groups include methylamino (—NH—$CH_3$); ethylamino (—$NHCH_2CH_3$), hydroxyethylamino (—NH—$CH_2CH_2OH$), and the like.

The term "aminoalkylamino" as used herein refers to an alkylamino group in which the alkyl portion is substituted with an additional amino group.

The term "hydroxyalkylamino" as used herein refers to an alkylamino group in which the alkyl portion is further substituted with a hydroxyl group.

The term "polyhydroxyalkylamino" as used herein refers to an alkylamino group in which the alkyl portion is further substituted with two or more hydroxyl groups.

The terms "dialkylamine" and "dialkylamino" as used herein refer to a moiety comprising a nitrogen atom substituted with two organic radicals that can be the same or different, which may be selected from but are not limited to aryl, substituted aryl, alkyl, substituted alkyl or arylalkyl, wherein the terms have the same definitions found throughout. Some examples include dimethylamino, methylethylamino, diethylamino and the like.

The term "dialkylaminoalkyl" as used herein refers to a dialkylamino group in which the amino portion is substituted upon an additional alkyl group.

The term "dialkylaminoalkylamino" as used herein refers to a dialkylamino group in which the amine portion is substituted upon an additional alkyl group, and that additional alkyl group is further substituted upon a second amino group.

The term "acylamino" as used herein refers to a moiety having the structure R—C(=O)N($R^1$)$R^2$, wherein R, $R^1$ and $R^2$ represent hydrogen or an alkyl group.

The term "N-morpholino" as used herein refers to a substituent in which the nitrogen atom of morpholine [6-member ring —N—($CH_2$)—($CH_2$)-0-($CH_2$)—($CH_2$)-] is bonded to an organic moiety.

The term "sulfamyl" as used herein refers to a group represented by the structure —S(=O)$_2$$NH_2$, and includes both unsubstituted sulfamyl groups and those substituted with an alkyl group at the N atom.

The term "alkylthio" as used herein refers to a —S—R substituent in which R is an alkyl group.

The term "alkylsulfide" as used herein refers to a —R—S—R' substituent in which R and R' are independently alkyl groups.

The term "mercapto" as used herein refers to a —S—H substituent.

The term "alkylsulfinyl" as used herein refers to a —S(=O)—R group, wherein R is an alkyl group.

The term "alkylsulfonyl" as used herein refers to a —S(=O)2-R group, wherein R is an alkyl group.

The term "carbalkoxy" as used herein refers to a —C(=O)-0-R group, wherein R is an alkyl group.

The term "carbamido" as used herein refers to ($NH_2$)$_2$CO in which at least one of the hydrogen atoms is replaced by a bond to an organic moiety.

The term "cation" as used herein refers to a species bearing a positive charge of 1+ or higher. Such cations include but are not limited to the alkali metal cations, alkaline earth metal cations, transition metal cations, ammonium salts, sulfonium salts, phosphonium salts, cycloheptatrienyl cations, hydroazulenium, and other positively charged species.

The term "ester" as used herein is represented by the formula —C(O)OR, where R can be an alkyl, halogenated alkyl, alkenyl, alkynyl, aryl, heteroaryl, cycloalkyl, cycloalkenyl, heterocycloalkyl, or heterocycloalkenyl group described above.

The terms "carboxyl" and "carboxylic acid" as used herein refer to a moiety having the formula —C(O)OH.

The term "carbonyl group" as used herein is represented by the formula C=O.

Representative compounds of this invention are as follows: 5-hydroxy-2-methyl-1-p-methylsulfinylbenzylidene-3-indene acetic acid; 5-methoxy-2-methyl-1-p-methylsulfinylbenzylidene-3-indene acetic acid; 5-fluoro-2-methyl-1-p-methylsulfinylbenzylidene-3-indene acetic acid; 5-fluoro-2-methyl-1-p-methylthiobenzylidene-3-indene acetic acid; 5-fluoro-2-methyl-1-p-methylsulfonylbenzylidene-3-indene acetic acid; α-5-fluoro-2-methyl-1-p-methylsulfinylbenzylidene-3-indene) propionic acid; 5,6-difluoro-2-methyl-1-p-methylsulfinylbenzylidene-3-indene acetic acid; 5-chloro-2-methyl-1-p-methylsulfinylbenzylidene-3-indene acetic acid; 5-trifluoromethyl-2-methyl-1-p-methylsulfinyl benzylidene-3-indene acetic acid; 5-methyl-2-methyl-1-p-methylsulfinylbenzylidene-3-indene acetic acid; 5,7-difluoro-2-methyl-1-p-methylsulfinylbenzylidene-3-indene acetic acid; α-(5,7-difluoro-2-methyl-1-p-methylsulfinylbenzylidene-3-indene) propionic acid; 5-dimethylamino-6-fluoro-2-methyl-1-p-methylsulfinylbenzylidene-3-indene acetic acid; 5-methoxy-6-fluoro-2-methyl-1-p-methylsulfinylbenzylidene-3-indene acetic acid; α-(5-methoxy-6-fluoro-2-methyl-1-p-methylsulfinylbenzylidene-3-indene) propionic acid; α-(5,6-difluoro-2-methyl-1-p-methylsulfinyl benzylidene-3-indene) propionic acid; 5-methoxy-2-methyl-1-p-methylsulfonylbenzylidene-3-indene acetic acid; 5,6-difluoro-2-methyl-1-p-methylsulfonylbenzylidene-3-indene acetic acid; 5,7-difluoro-2-methyl-1-p-methylsulfonylbenzylidene-3-indene acetic acid; 5-dimethylamino-6-fluoro-2-methyl-1-p-methylsulfonylbenzylidene-3-indene acetic acid; 5-methoxy-6-fluoro-2-methyl-1-p-methylsulfonylbenzylidene-3-indene acetic acid; α-(2-methyl-5,6-difluoro-1-p-methylsulfonylbenzylidene-3-indene) propionic acid; and the corresponding amides, esters and salts.

The compounds of the invention may be isomerized into their cis and trans isomers by procedures well known in the art. The cis isomer of the compounds is substantially more active than the trans isomer. Accordingly, the compounds of the invention are intended to encompass not merely the compounds per se but includes their geometric isomers (cis, trans).

The alkylsulfinyl, alkylsulfide, alkylthio, or alkylsulfonyl derivatives can be racemic mixtures of optically active enantiomorphs which may be resolved into their (+) and (−) forms by techniques well known in the art. Furthermore, when R1 is lower alkyl an additional asymmetric atom results which gives rise to two additional enantiomorphs. Some compounds of the invention are polymorphic and have different crystalline structures, melting points and solubility characteristics.

In a particular embodiment, the "sulindac derivatives" are Phospho-sulindac compounds of general formula IV wherein M represents a loweralkoxy group substituted by a phosphate ester group (—O—P(=O)(OR$_x$)$_2$ wherein R$_x$ is an H, alkyl, alkenyl, alkynyl, aryl or an aralkyl group, which may in turn be substituted or unsubstituted.

The term "phospho" when used refers to one or more —OP(=O)(OR$_x$)$_2$ functional groups, wherein R$_x$ may be hydrogen or any substituent set forth herein.

A substituent may be a halogen (i.e., F, Cl, Br, and I); an alkyl group, such as methyl, ethyl, n-propyl, iso-propryl, n-butyl, tert-butyl, and trifluoromethyl; hydroxyl; an alkoxy group, such as methoxy, ethoxy, n-propoxy, and iso-propoxy; an aryloxy group, such as phenoxy; arylalkyloxy, such as benzyloxy (phenylmethoxy) and p-trifluoromethylbenzyloxy (4-trifluoromethylphenylmethoxy); a heteroaryloxy group; a sulfonyl group, such as trifluoromethanesulfonyl, methanesulfonyl, and p-toluenesulfonyl; nitro, nitrosyl; mercapto; a sulfanyl group, such as methylsulfanyl, ethylsulfanyl and propylsulfanyl; cyano; an amino group, such as amino, methylamino, dimethylamino, ethylamino, and diethylamino; carboxyl, phosphate or phosphate ester (—OP(=O)(OR$_x$)2).

In a particular embodiment, the loweralkoxy group of the present invention is a C1-C6 alkoxy group, preferably a C1-C4 alkoxy group.

Sulindac derivatives are described in WO2009/023631, WO2011/130486, Cheng et al., 2013, and Zhou et al., 2010. Examples of Phospho-sulindac compounds are the following:

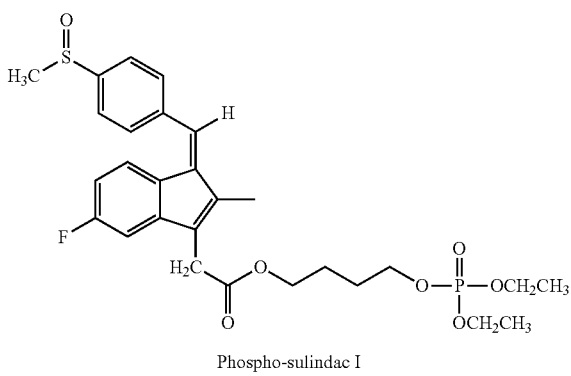

Phospho-sulindac I

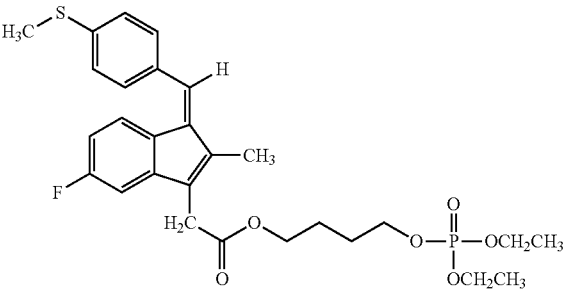

Phospho-sulindac II

In one embodiment, sulindac derivatives improve the effect of sulindac on its therapeutic targets, improve its pulmonary bioavaibility, and improve its solubility in formulation capable of being administered by nasal administration or by inhalation.

The present invention also relates to sulindac or sulindac derivatives for use in the treatment of inflammatory pulmonary diseases in a subject in need thereof.

The present invention also relates to sulindac or sulindac derivatives in combination with one or more anti-cystic fibrosis agent for use in the treatment of cystic fibrosis in a subject in need thereof.

The present invention also relates to sulindac or sulindac derivatives in combination with one or more anti-inflammatory agent for use in the treatment of inflammatory pulmonary diseases in a subject in need thereof.

In one embodiment, the anti-cystic fibrosis agent or anti-inflammatory agent may include a CFTR corrector or potentitator (Kalydeco), osmotic agents (Bronchitol), antioxidants drugs, modifier of mucus (Pulmozyme, Mucomyst . . . ), bronchodilatators (Ventolin, Serevent . . . ), anti-infective compounds (TOBI, Azithromycin, Josacine, . . . ) or further anti-inflammatory drugs (Ibuprofen, Dexamethasone, Zyflo, Accolate . . . ).

The present invention also relates to a method for treating cystic fibrosis in a subject in need thereof, comprising the step of administering to said subject the sulindac or a sulindac derivatives.

The present invention also relates to a method for treating inflammatory pulmonary diseases in a subject in need thereof, comprising the step of administering to said subject the sulindac or a sulindac derivatives.

The present invention also relates to a method for treating cystic fibrosis in a subject in need thereof, comprising the step of administering to said subject the sulindac or a sulindac derivatives in combination with one or more anti-cystic fibrosis agent.

The present invention also relates to a method for treating inflammatory pulmonary diseases in a subject in need thereof, comprising the step of administering to said subject the sulindac or a sulindac derivatives in combination with one or more anti-inflammatory agent.

Pharmaceutical Composition

The compound of the invention may be used or prepared in a pharmaceutical composition.

In one embodiment, the invention relates to a pharmaceutical composition comprising the compound of the invention and a pharmaceutical acceptable carrier for use in the treatment of cystic fibrosis in a subject in need thereof.

Typically, the compound of the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, inhalation, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, inhalation administration forms, aerosols, implants, subcutaneous, transdermal, topical, intraperitoneal, intramuscular, intravenous, subdermal, transdermal, intrathecal and nasal or intranasal administration forms and rectal administration forms.

Preferably, the pharmaceutical compositions contain vehicles which are pharmaceutically acceptable for a formulation capable of being administered by nasal administration or by inhalation. Nasal administration may be under the form of liquid solution, suspension or emulsion. Solutions and suspensions are administered as drops. Solutions can also be administered as a fine mist from a nasal spray bottle or from a nasal inhaler. Inhalation may be accomplished under the form of solutions, suspensions, and powders; these formulations are administered via an aerosol, droplets or a dry powder inhaler. The powders may be administered with insufflators or puffers.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The compound of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

In another embodiment, the invention relates to a pharmaceutical composition comprising the compound of the invention and a pharmaceutical acceptable carrier for use in the treatment of inflammatory pulmonary disease in a subject in need thereof.

Pharmaceutical compositions of the invention may include any further agent which is used in the prevention or treatment of cystic fibrosis or pulmonary inflammatory disease. For example, pharmaceutical compositions of the invention can be co-administered with CFTR corrector or potentitator (Kalydeco), osmotic agents (Bronchitol), antioxidants drugs, modifier of mucus (Pulmozyme, Mucomyst . . . ), bronchodilator agents (Ventolin, Serevent . . . ), anti-infective compound (TOBI, Azithromycin, Josacine, . . . ) or with other anti-inflammatory drugs (Ibuprofen, Dexamethasone, Zyflo, Accolate . . . ).

The invention will be further illustrated by the following figures and examples. However, these examples and figures should not be interpreted in any way as limiting the scope of the present invention.

FIGURES

FIG. 1: Sulindac Suppresses NF-κB Transcriptional Activity.

All cells were transiently transfected by NF-κB firefly luciferase reporter and renilla luciferase reference. A. HeLa control cells (Ctr) were pre-treated with diluent (0.5%) or different doses of sulindac for 1 h and stimulated for 1 h with 10 ng/ml TNFα. After removal of TNFα, cells were incubated for 4 h with sulindac. Luciferase activity was analysed in protein extract. The NF-κB transcriptional activity in cells treated with sulindac+TNFα was expressed in percent of diluent+TNFα. B. Hela cells Wt, DF508 and Ctr were pre-treated with diluent (0.5%), ibuprofen (500 µM) or sulindac (500 µM) for 1 h and stimulated for 1 h with 10 ng/rill TNFα. After removal of TNFα, cells were incubated for 4 h with pharmacological treatment. The NF-κB transcriptional activity in cells treated with ibuprofen+TNFα and sulindac+TNFα was expressed in percent of diluent+TNFα. Results of at least three independent experiments, means±SEM. Unilateral paired t test: * $p<0.02$ FIG. 2: Sulindac Down Regulates IL-8 Production Unlike Ibuprofen.

Cells were transiently transfected by the short IL-8 promoter-firefly luciferase reporter and renilla luciferase reference and inflammation was induced by 10 ng/ml TNFα for 1 h. A. HeLa cells were pre-treated with diluent or different doses of sulindac 1 h before inflammation induction and 4 h after. IL-8 promoter activity in cells treated with sulindac+TNFα was expressed in percent of diluent+TNFα. B. After treatment, HeLa Ctr cells were lysed with TRIzol (Invitrogen). Total RNA was extracted, and 1 µg of total RNA was reverse transcribed with a reverse transcription kit. IL-8 mRNA expression was quantified by real-time quantitative PCR (qPCR). The comparative threshold cycle ($C_T$) method was used for relative quantification of PCR products after IL-8 was normalised to TBP ($\Delta Ct=Ct_{IL-8}-Ct_{TBP}$). IL-8 mRNA data in treated samples were expressed in fold changes over controls: fold change$_{treated\ sample}=2^{-\Delta\Delta Ct}$ (with $\Delta\Delta Ct=\Delta C_{treated\ sample}-\Delta Ct_{control}$). C After treatment, IL-8 in supernatant was measured by ELISA. The IL-8 stimulation of cells treated with test drug +TNFα were expressed as fold compared to drug −TNFα. Results of three independent experiments, means±SEM. Unilateral paired t test: * $p<0.02$, ** $p<0.01$.

Figure 3:
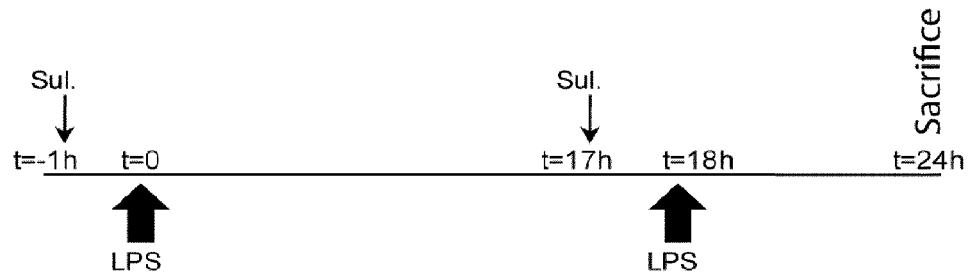
Figure 3:
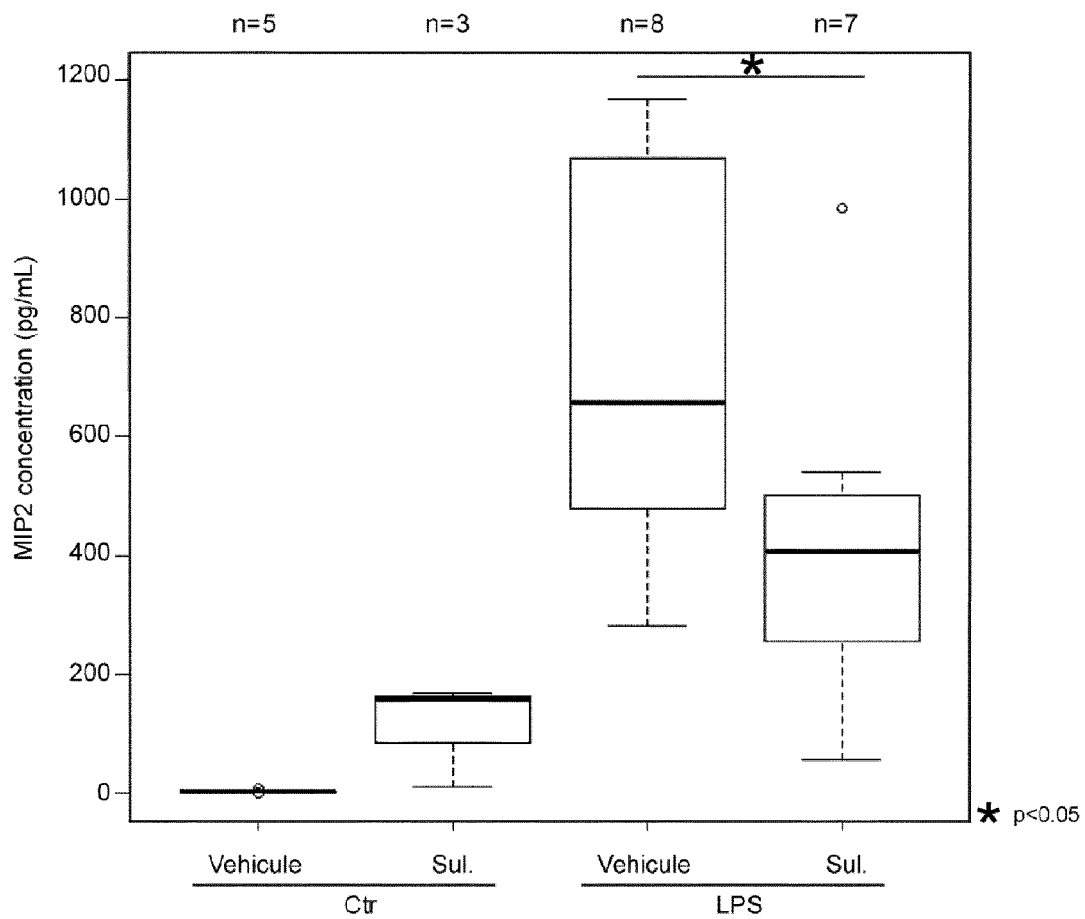

FIG. 3: Sulindac Down Regulates MIP-2 Production in BAL in ALI Mouse Model.

A. Protocol for lung inflammation mouse models. Lung inflammation was induced by two intra tracheal instillation of LPS (5 mg/kg), 24 h and 6 h prior sacrifice. Sulindac (40 mg/kg) or diluents were administered by intraperitoneal injection 1 h before LPS instillation. B. Mouse macrophage inflammatory protein (MIP-2) was monitored in BAL fluid by ELISA assay. LPS-stimulated MIP-2 production was inhibited by sulindac.

Figure 4A:
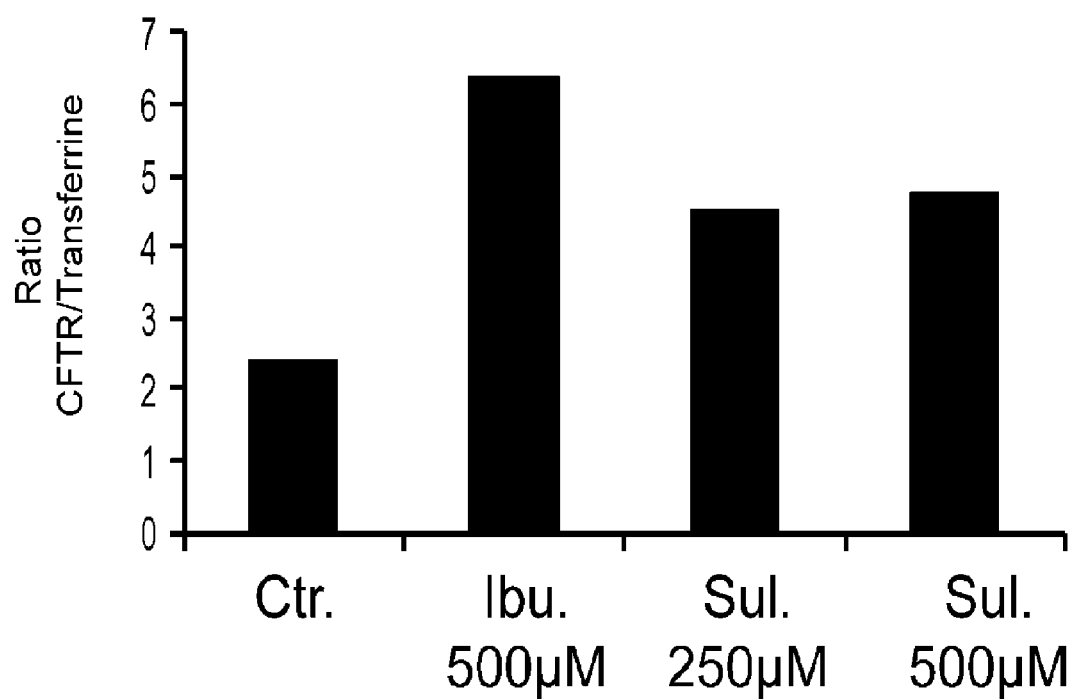
Figure 4B:
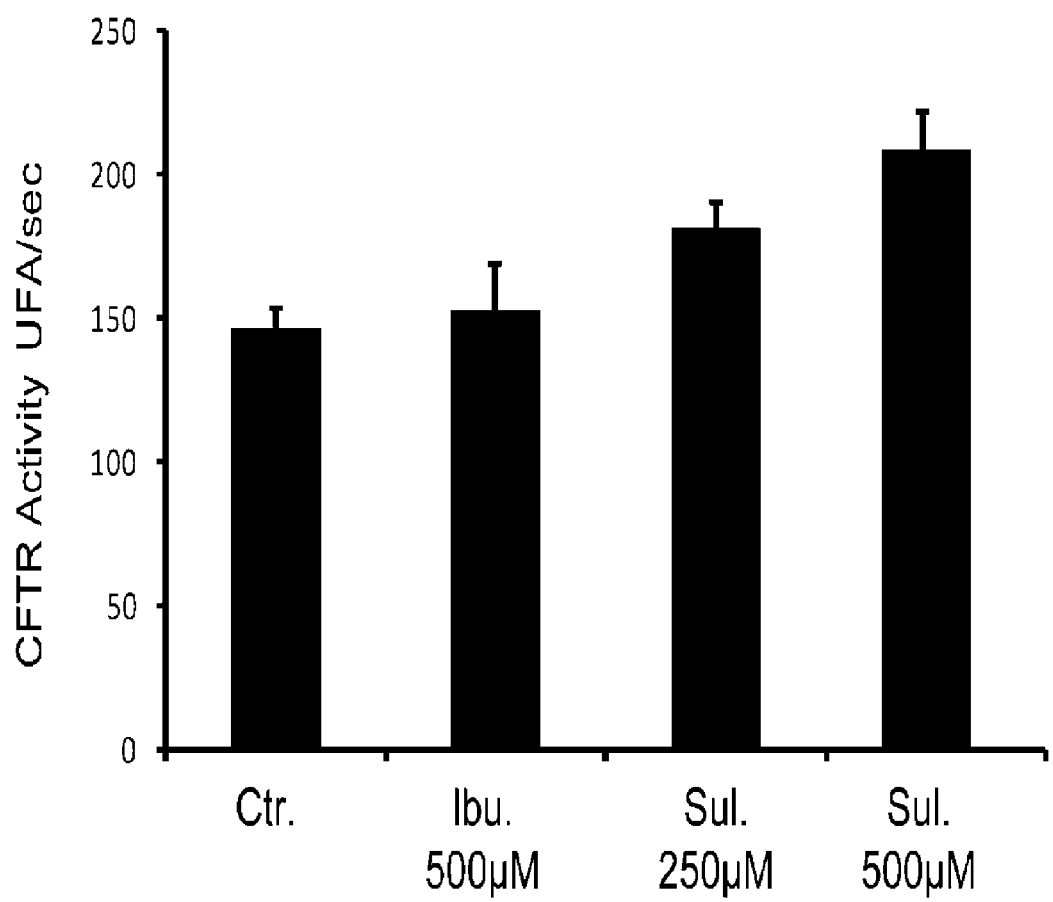
Figure 4C:
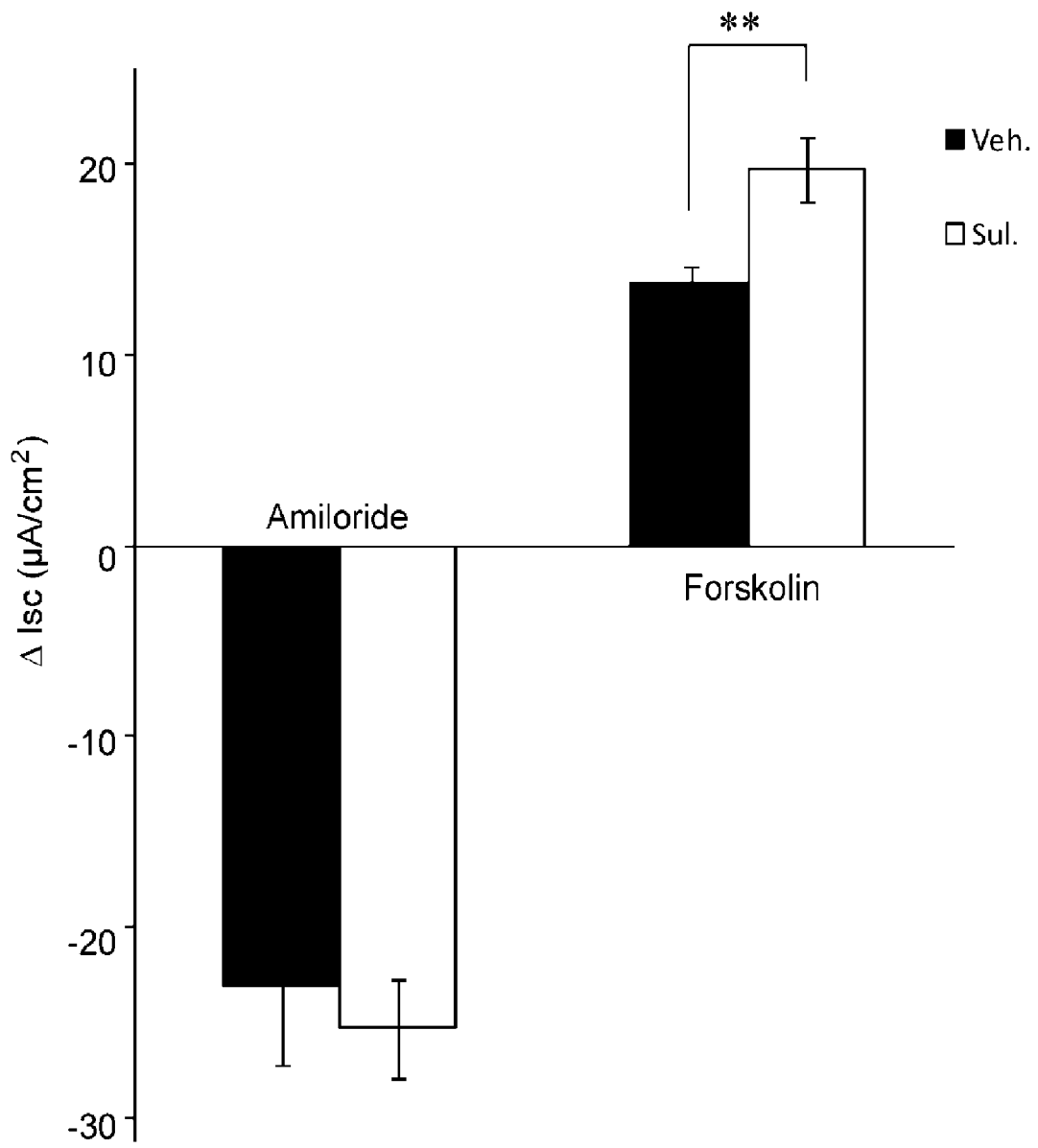

FIG. 4: Sulindac Induces the Increase of CFTR Chloride Activity.

A. In WT-CFTR HeLa cells, treatment with sulindac and ibuprofen (500 µM) induces a significant increase of mature form of CFTR visualized by Western blot. B. Chloride activity in HeLa Wt cells was measured by MQAE assay, after 3 h of treatment by NSAID (500 µM) or diluent. CFTR activity was expressed in rate of UFA/sec, calculated by difference between ((Ft−F0)/t) with CFTR induction and ((Ft−F0)/t) without CFTR induction. Unlike ibuprofen, sulindac induced an increase of CFTR activity about 30%. C. Primary culture of human nasal epithelial cell (HNEC) grown on Snapwell filters (air-liquid interface) were exposed basolaterally to sulindac (500 µM) or vehicle for 2 h and immediately mounted into a voltage-clamp system to bioelectric measurements. Short circuit current was measured with addition of amiloride to evaluated amiloride sensitive transport or with forskolin and IBMX for induced cAMP-dependent Cl secretion. Sulindac not induced modification of ENaC activity but induced 46.35%±17.2 increase of CFTR activity. The values are the means SEM of five filters for each condition. **, significantly different from control ($p<0.01$).

Figure 5:
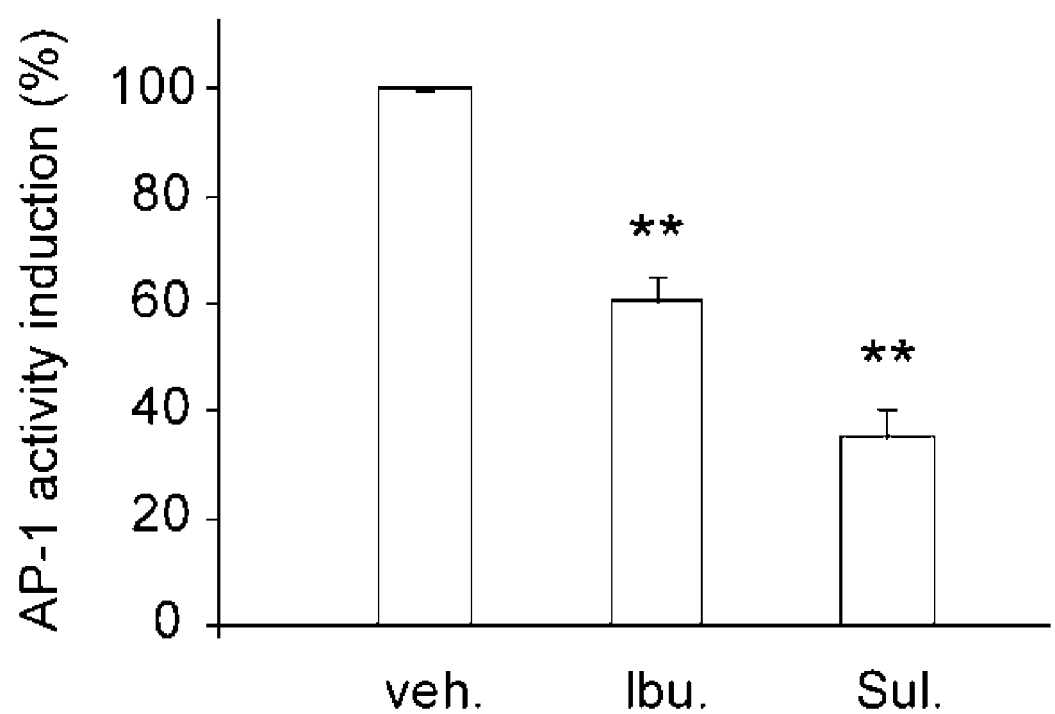

FIG. 5: Sulindac Down Regulates AP-1 Transcriptional Activity.

HeLa cells were transiently transfected by AP-1 firefly luciferase reporter and renilla luciferase reference. HeLa control cells were pre-treated with diluent (0.5%), ibuprofen (500 µM) or sulindac (500 µM) for 1 h and stimulated for 1 h with 10 ng/ml TNFα. After removal of TNFα, cells were incubated for 4 h with pharmacological treatment. The AP-1 transcriptional activity in cells treated with ibuprofen+TNFα and sulindac +TNFα was expressed in percent of diluent+TNFα. Results of three independent experiments, means±SEM. Unilateral paired t test: ** $p<0.01$.

Figure 6:
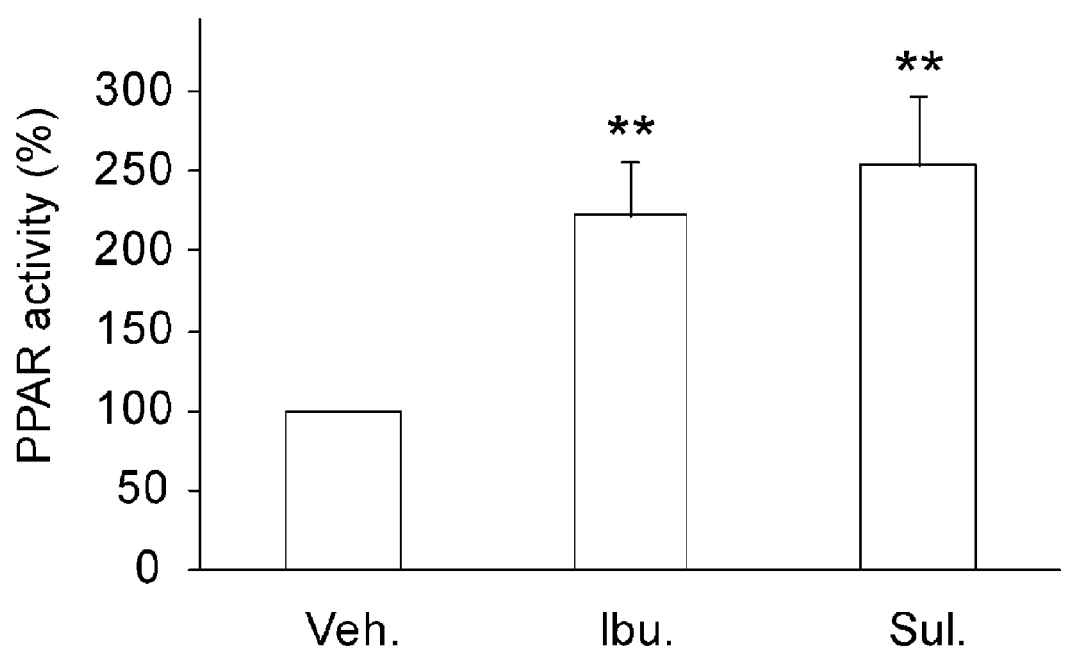

FIG. 6: Sulindac Induced PPAR Transcriptional Activity.

HeLa control cells were transiently transfected by PPAR firefly luciferase reporter (3 PPRE motifs) and renilla luciferase reference. Cells were treated with diluent (0.5%), ibuprofen (500 µM) or sulindac (100 µM) for 24 h. The PPAR transcriptional activity in cells treated with ibuprofen and sulindac was expressed in percent of diluents. Results of three independent experiments, means±SEM. Unilateral paired t test: ** $p<0.01$.

Figure 7:
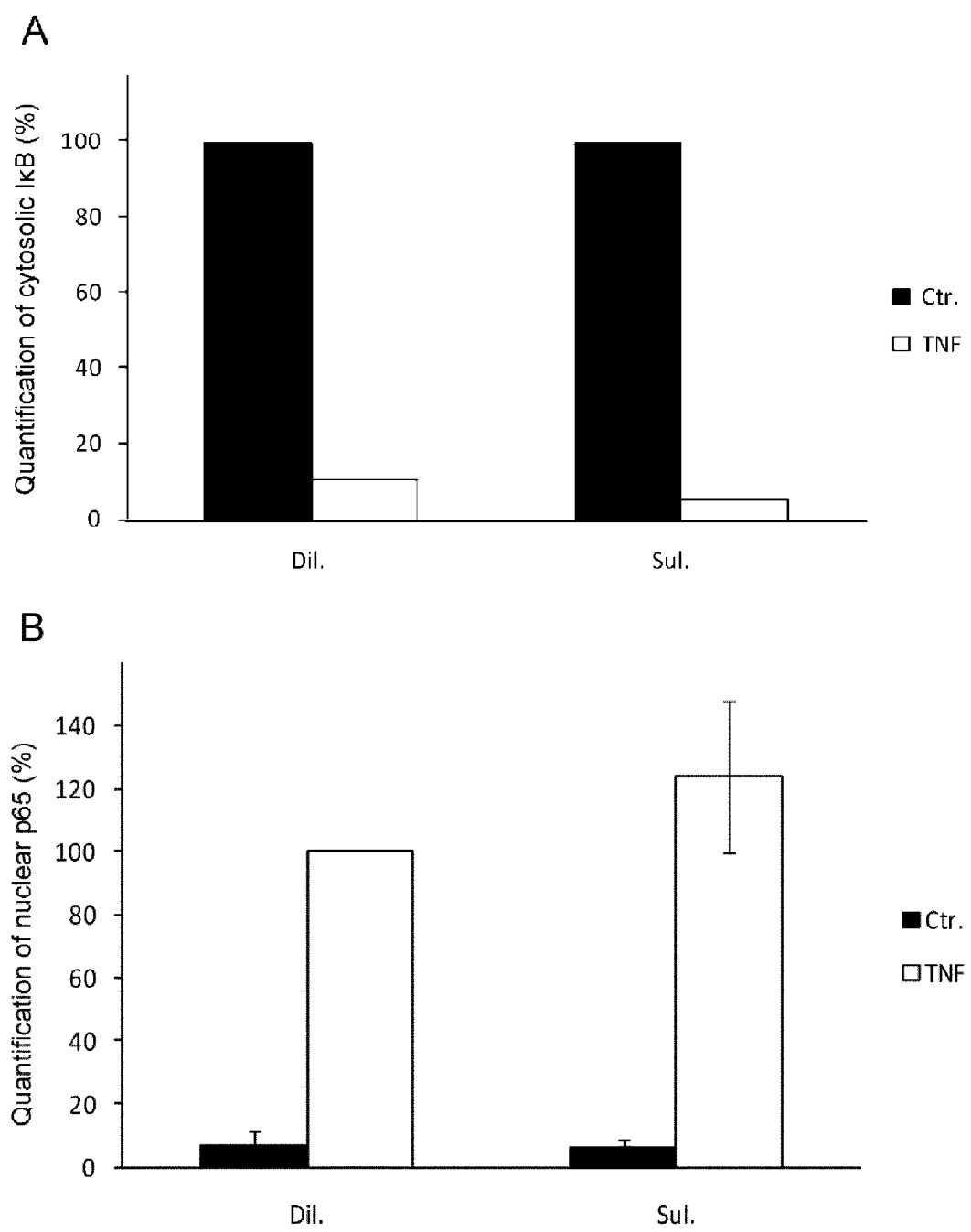

FIG. 7: Sulindac does not Inhibit Nuclear Translocation of NF-κB.

HeLa control cells were pre-treated with diluent (0.5%) or sulindac (500 µM) for 1 h and stimulated or not with 10 ng/ml TNFα for 30 min. Nuclear and cytosolic fractions were obtained by differential centrifugation. A. Analysis by western blot of cytosolic IKb quantity. The Iκb quantity was expressed in percent of control. TNFα induced a rapidly degradation of Iκb (more 90%) and the pre-treatment with sulindac did not modified this effect. B. Analysis by western blot of nuclear p65 quantity. Nuclear p65 quantity was expressed in percent of diluents+TNFα. Inflammation induced rapidly nuclear translocation of p65 that was not significantly modified by sulindac.

Figure 8:
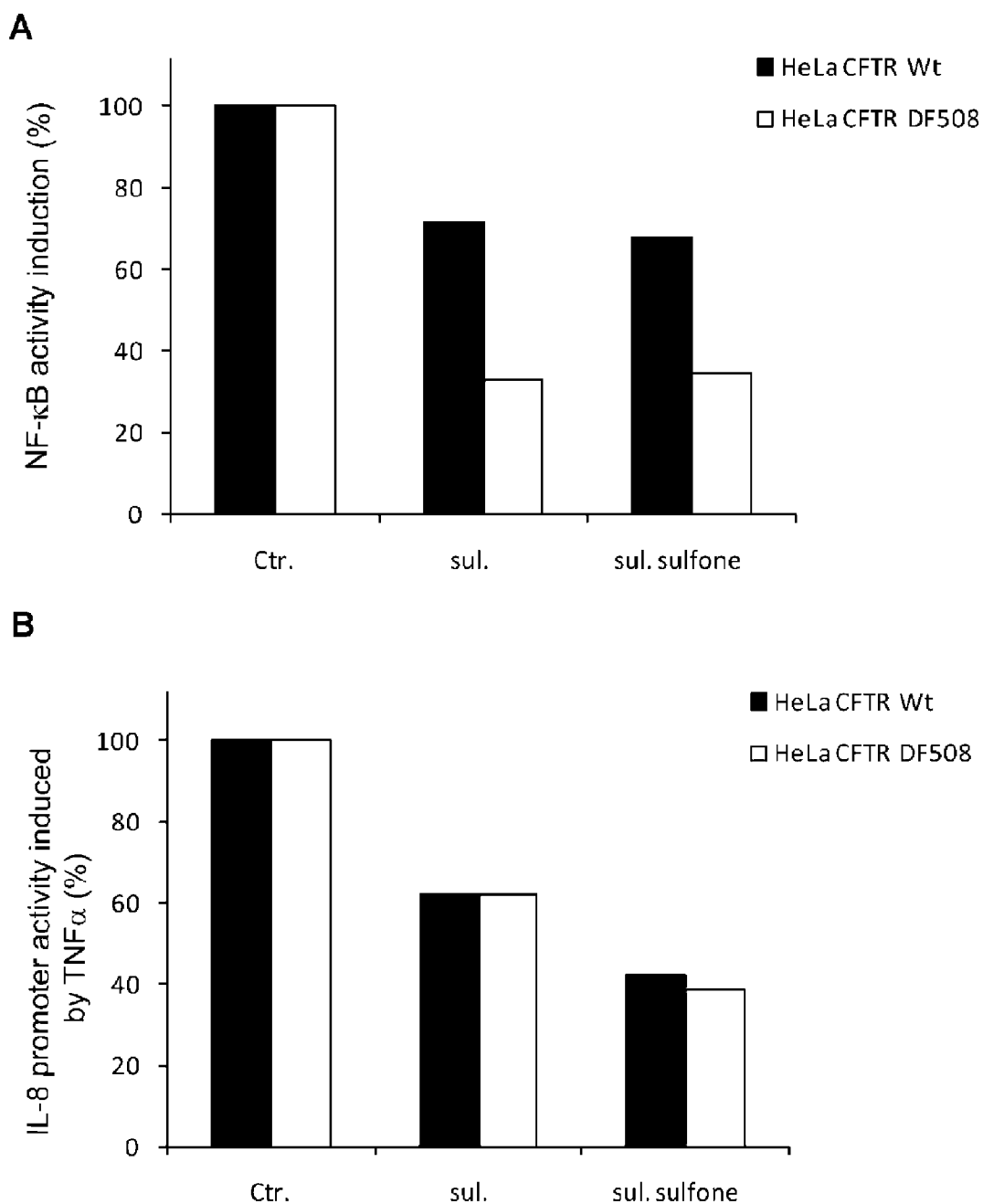

FIG. 8: The Effects of Sulindac on NF-κB and IL-8 are Independent of that Anti-COX Activity.

All cells were pre-treated with diluent (0.5%), sulindac (250 W) or sulindac sulfone (250 µM) for 1 h and stimulated for 1 h with 10 ng/ml TNFα. After removal of TNFα, cells were incubated for 4 h with pharmacological treatment. A. HeLa CFTR wt and CFTR DF508 cells were transiently transfected by NF-κB firefly *luciferase* reporter and *renilla luciferase* reference. The NF-κB transcriptional activity in cells treated with sulindac or sulindac sulfone was expressed in percent of diluents. In all cells, sulindac sulfone and sulindac have similar activity on NF-κB. B. HeLa CFTR wt and CFTR DF508 cells were transiently transfected by the short IL-8 promoter-firefly *luciferase* reporter and *renilla luciferase* reference. IL-8 promoter activity in cells treated with sulindac and sulindac sulfone was expressed in percent of diluents. In all cells, sulindac sulfone is at least as effective as sulindac with respect to inhibition of the induction of IL-8.

EXAMPLE 1

Material & Methods

All reagents were purchased from Sigma (St. Louis, Mo.) unless otherwise specified. C57BL/6J mice were purchased from Janvier (France). Sulindac and ibuprofen were prepared as stocks in DMSO (100 mM) and stored at −20° C. DMSO was used as a diluent control in these experiments.

Cell Culture and Treatments.

The inventors used for these studies a heterologous model of stable HeLa that expressed:
the wild type CFTR protein, cell line spTCF-wt (Wt)
the mutant CFTR protein ΔF508, cell line spTCF-ΔF508 (delta F508)
and the control cell lines, the cell line spTracer (Ctr) [14]
Three others models were used to study IL-8 regulation and the canal chloride activity of CFTR.
BEAS-2B cells, an epithelial cell line which low expression of CFTR, used to confirmed transcriptional assay in epithelial cells.
Two cell models were used to the interface air-liquid model for ionic efflux assays by short circuit current and to dose the basolateral IL-8 secretion. Calu-3 are derived from lung adenocarcinoma and are able to polarized and express a high rate of endogenous CFTR. The inventors also used primary cultures of human nasal epithelial cell (HNEC), which are nasal polyp cells and which express CFTR. Nasal polyps were obtained from non-CF requiring surgery for their nasal polyposis. This protocol was approved by the Institutional Review Board and ethics committee of our institution (CCP-PRB, Hopital Henri Mondor), and informed consent was obtained from all patients. Nasal polyp samples were immediately placed in DMEM/Ham's F-12 supplemented with antibiotics mix (100 units/mi of penicillin, 100 mg/ml of streptomycin, 2.5 g/ml of amphotericinB, and 100 mg/ml of gentamicin) and transported to the laboratory for cell isolation. Briefly, nasal polyp samples were rinsed in phosphate-buffered saline (PBS) with dithiothreitol (5 nM) and antibiotics mix and then placed overnight at 4° C. in a PBS antibiotics solution containing 0.1% Pronase. Finally, HNEC were plated on permeable polycarbonate supports Snapwell (Costar, Cambridge, Mass.) at $10^6$ cells/cm² for short circuit current measurements. All inserts were coated with type IV collagen. HNEC were incubated at 37° C. in 5% $CO^2$. For the first 24 hours, HNEC were incubated with 1 ml of DMEM/Ham's F-12 antibiotics with 2% Ultroser G outside the insert and DMEM/Ham's F-12 antibiotics with 10% fetal calf serum inside the insert. After, the medium was removed inside the inserts to place the cells at an air-liquid interface, and the medium outside the inserts was then changed daily. Transepithelial resistance and transepithelial potential difference were measured every 3 days using a microvoltmeter (World Precision Instruments, Astonbury, UK).

Cells were grown at 37° C. in a 5% $CO_2$ incubator in DMEM with Glutamax (Invitrogen) and 10% fetal bovine serum (SVF). Nasal polyp cells were maintained in Ham's F-12 (F-12) nutrient medium and Dulbecco's modified Eagle's nutrient mixture (DMEM), penicillin, streptomycin, amphotericin B, fetal calf serum (FCS), trypsin, EDTA, and Ultroser G (Invitrogen). For the treatment, drugs were added in DMEM 1% SVF in order to reduce drug aggregation with the proteins contained in SVF. The effects of treatment in HNEC cultures on snapwell inserts were evaluated between days 10 and 16. The cells were treated with 500 nM of sulindac added to the basolateral side or with vehicle (control cells) for 1 or 4 hours.

Plasmid Constructs and Transient Transfection To assay the transcriptional activity of NF-κB, pNF-κBLuc, a *luciferase* reporter plasmid containing five sequential NF-κB binding sites upstream of a minimum promoter element, NF-κB-Luc (Stratagene), was used. Transcriptional activity of the IL-8 promoter was evaluated with reporter constructs consisting of the IL-8 promoter (−133 bp from the transcription start site) fused to the *Luciferase* gene, kindly provided by Naofumi Mukaida [15]. Cells ($1.2 \times 10^5$ cells/cm²) were transfected with the turbofect reagent (Fermentas), according to the manufacturer's protocol. To normalize transfection efficiency, a *renilla luciferase* reporter construct (pRL-TK, Promega) was co-transfected with each of the firefly *luciferase* constructs. 48 hours after transfection, cells were exposed to TNFα (10 ng/mL) for 1 hour. Cells were pre- and treated with sulindac, ibuprofen or vehicule control one hour before and four hours after this induction.

*Luciferase* Assay

Cells were lysed with the Passive Lysis Buffer (Promega), and *luciferase* activity in the cellular extracts was determined by the Dual *Luciferase* Assay System (Promega) using a luminometer (Tristar; Berthold). The results were normalized to those obtained with the *Renilla luciferase* reference plasmid used to control the transfection efficiency, and the values were expressed as luminescence intensity (*Luciferase/Renilla*). In each experiment, the results were compared to a control condition to which the value of 1 RLU (RLU: Relative Light Unit) was arbitrarily assigned. Data shown are the means (±SEM) of at least three independent experiments.

Assays for IL-8 Release

IL-8 secretion into the supernatant of cells cultures was measured with the IMMULITE 1000 Automated Analyser (Diagnostic Products Corp) and the commercially available Immulite chemiluminescent enzyme immunometric assays (Immulite®) according to the manufacturer's instructions.

Mouse and Animals Experiments

Male C57BL/6J mice (8-10 wk old) were treated by intra-peritoneal (IP) injection of sulindac (40 mg/kg) or vehicle one hour before the time of endotoxin administration which caused lung injury. Lung inflammation was induced by LPS from *E. coli* (Sigma) prepared in saline and administered by injection intra-tracheal. In order to track at a single time point after LPS challenge both the early humoral and the late cell infiltrating components of the inflammatory response, a volume of 50 µl LPS solution (5 mg/kg) was administered at two consecutive doses with a 18 h interval between doses. This challenge method enables to track both cytokine and cellular responses to induction of inflammation. The mice were killed six hour after the last LPS tracheal instillation. BAL (broncho alveolar lavage) was performed by cannulating the trachea and lavaging with 2 ml sterile saline. Differential cell counts were performed on cytospin. After centrifugation, the supernatant was stored at −80° C. for further biochemical measurements. The chemokines keratinocyte chemoattractant (KC) and mouse macrophage inflammatory protein (MIP-2) were monitored in BAL fluid following the corresponding manufacturers' protocols using a standard sandwich enzyme-linked immune absorbent assay (ELISA, R&D Systems).

Membrane Protein Extraction and Western Blot

To study the CFTR protein present at the cell membrane, a protocol of purification by differential centrifugations was used. CFTR wt and delta F508 HeLa cells ($2 \times 10^5$ cells/cm$^2$) were lysed with hypotonic lysis buffer (10 mM de KCl, 1 mM de $MgCl_2$, 10 mM Hepes pH 7, 4 and protease inhibitor). Mechanic lysis of cells was realized with minimum 10 strokes of a 26G syringe. Samples were centrifuged 10 min at 3000 g to eliminate cellular fragments and nuclear fraction in the pellet. Then supernatant was centrifuged 45 min at 50 000 g. The pellets with cellular membrane were resolubilized in RIPA buffer.

Aliquots of membrane cell extracts (30 µg protein) were separated by 7% SDS-PAGE and transferred on PVDF membrane. The western blots were probed with mouse monoclonal antibodies specific for CFTR (MM13-4, Millipore) 2 h at room temperature. After 1 hour of incubation with HRP anti-mouse antibodies, Chemioluminescence were revealed by ECL (GE Healthcare, Life Science) Gene GNOME camera (Syngene Bio Imaging).

Fluorescent Chloride Efflux Assay

Chloride efflux was determined using the fluorescent chloride indicator N(ethoxycarbonylmethyl)-6-methoxyquinolinium bromide (MQAE) (Invitrogen). HeLa Wt CFTR cells were grown to confluence in 96-well black plates with a clear flat bottom. After 3 hours of sulindac or ibuprofen treatment, cells were loaded for 45 min by hypotonic shock (buffer A/water 1:1 containing 10 mM MQAE) (buffer A: 20 µM Bumetamide, 2.4 mM $K_2HPO_4$, 0.8 mM $KH_2PO_4$, 1 mM $CaSO_4$, 10 mM glucose, 10 mM Hepes pH 7.6). Cells were incubated in a chloride buffer (buffer A+138 mM NaCl) and background fluorescence was recorded over 3 min with microplate reader (360 nm excitation/460 nm emission filter, Tristar, Berthold). After this, the buffer was changed to a chloride-free, nitrate-containing buffer (buffer A+138 mM $NaNO_3$) and increase fluorescence is monitored for 3 mM. Fluorescence was re-quenched with chloride buffer contained 50 µM CPT-cAMP to stimulate CFTR. The buffer was again changed for a nitrate buffer with CPT-cAMP and the increase fluorescence was recorded continuously in 10 s intervals for 5 min. At the end of the experiments, background fluorescence level was controlled with chloride buffer. To assess whether the efflux was CFTR dependant, experiments with 50 µM CFTRinh-72 were performed. Four separate wells were used for each group and activity of CFTR (arbitrary fluorescent units/sec) was evaluated comparing the difference between ((Ft−F0)/t) with and without CPT-cAMP. Data shown are the means (±SEM) of at least three independent experiments.

Electrophysiological Studies

Measurements of short circuit current ($I_{sc}$), transepithelial potential difference, and transepithelial resistance ($R_{te}$) were performed in cells treated by sulindac or vehicle. Snapwell inserts were mounted in vertical diffusion chambers and were bathed with Ringer solution (pH 7.4) continuously bubbled with 5% $CO^2$, 95% air at 37° C. The apical and basolateral chambers were filled with 137 mM NaCl, 5.6 mM KCl, 1.9 mM $CaCl_2$, 1.2 mM MgCl 2, 5.9 mM $CH_3CO_2Na$, 1.3 mM $NaH_2 PO^4$, 10 mM HEPES, and 10 mM glucose. Potential difference was short circuited to 0 mV with a voltage clamp (World Precision Instruments, Astonbury, UK) connected to the apical and basolateral chambers via Ag—AgCl electrodes and agar bridges to measure $I_{sc}$. $R_{te}$ was calculated by Ohm's law. $I_{sc}$ was allowed to stabilize, before adding the drugs. Amiloride (100 µM) was applied to the apical solution to calculate the amiloride-sensitive part of $I_{sc}$ ($I_{sc\ amil}$), which is the difference between $I_{sc}$ measured in the absence and presence of amiloride. Amiloride-treated HNEC were then stimulated with forskolin (10 µM, basolateral side) and IBMX (100 µM, basolateral side) to induce cAMP-dependent Cl secretion ($I_{sc\ IBMX forsk}$). $I_{sc\ IBMX forsk}$ was the difference between the initial value of $I_{sc}$ and the peak value obtained in response to drug addition. To assess whether the efflux was CFTR dependant, experiments with 50 µM CFTRinh-72 were performed. Data shown are the means (±SEM) of at least three independent experiments.

Results

Figure 2:
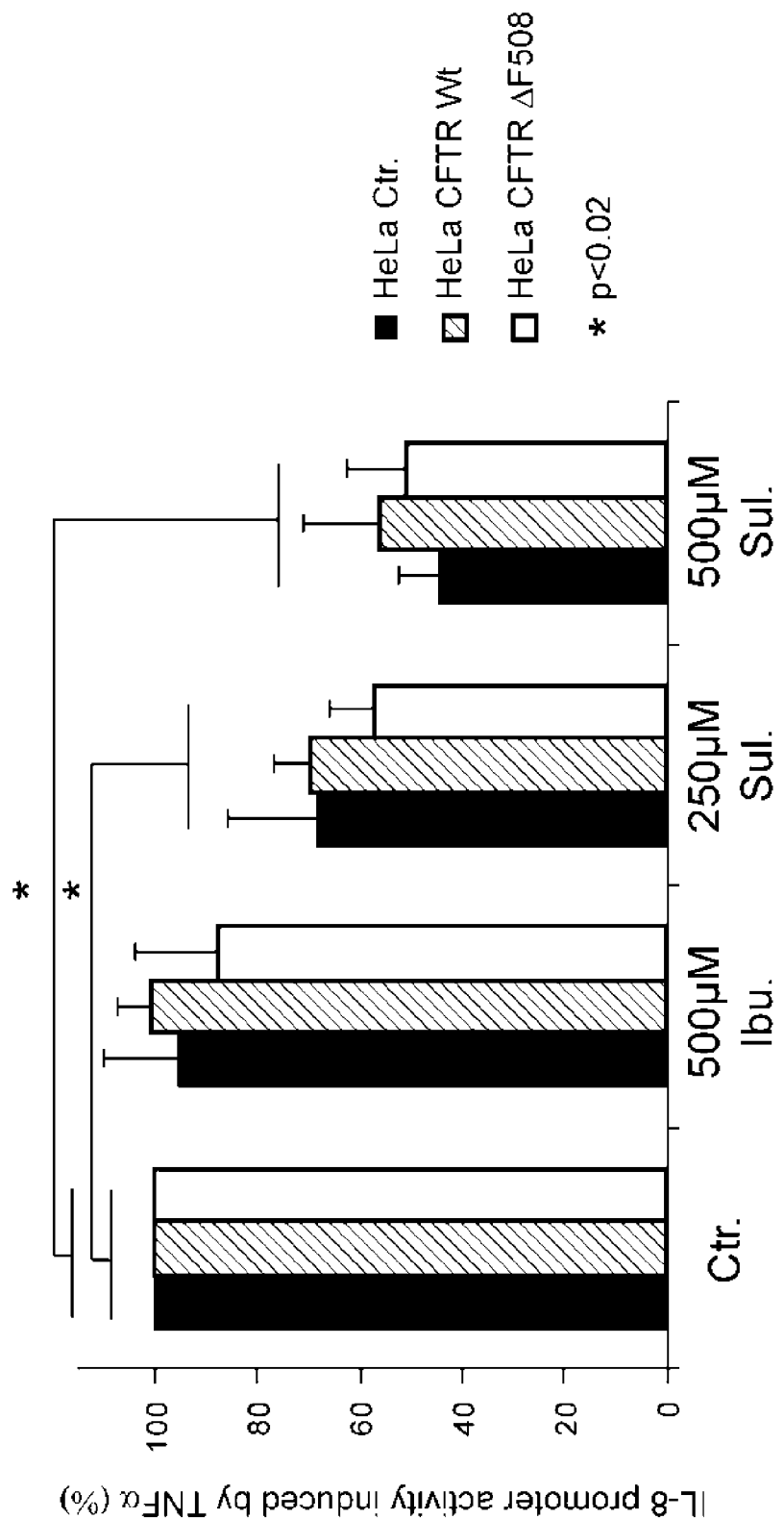
Figure 2:
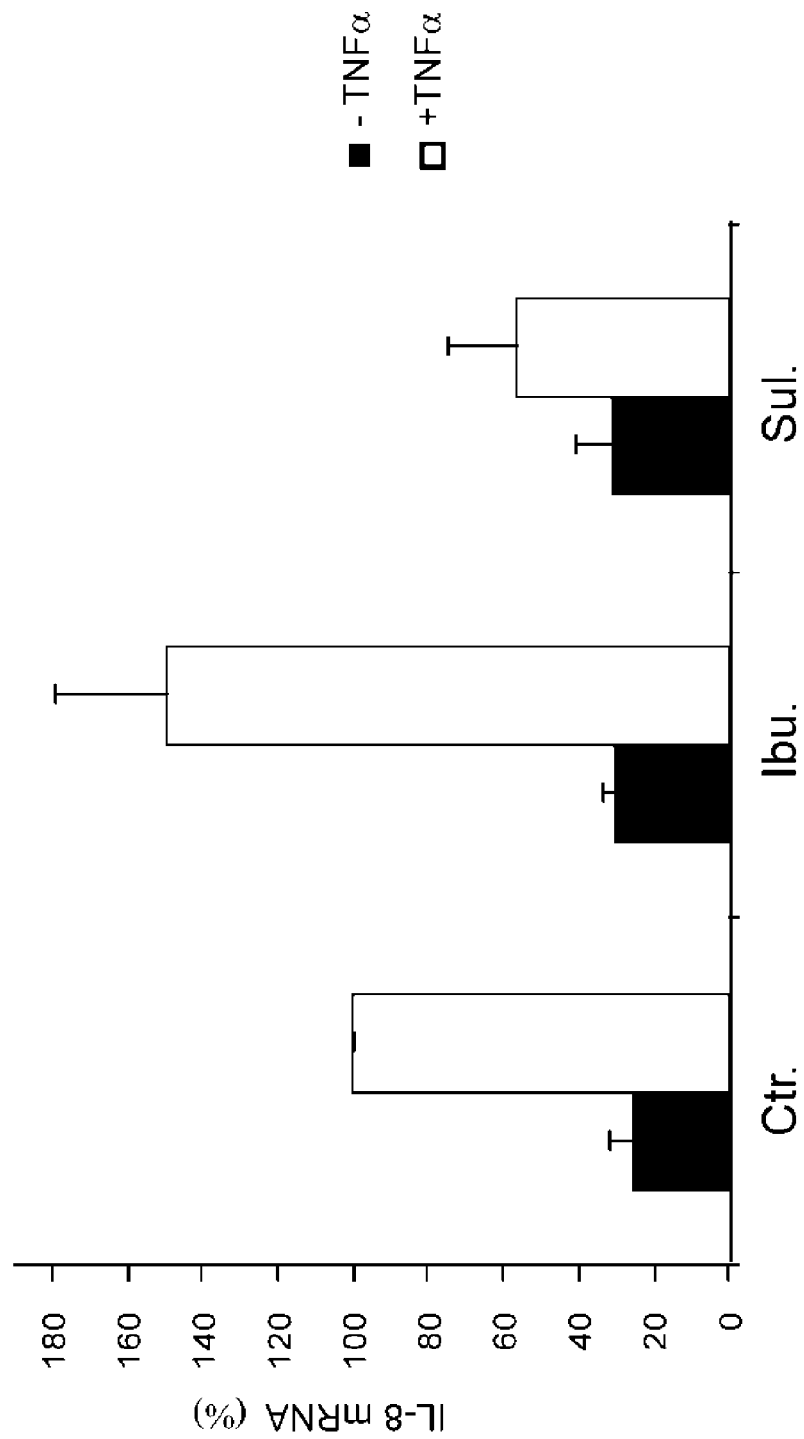
Figure 2:
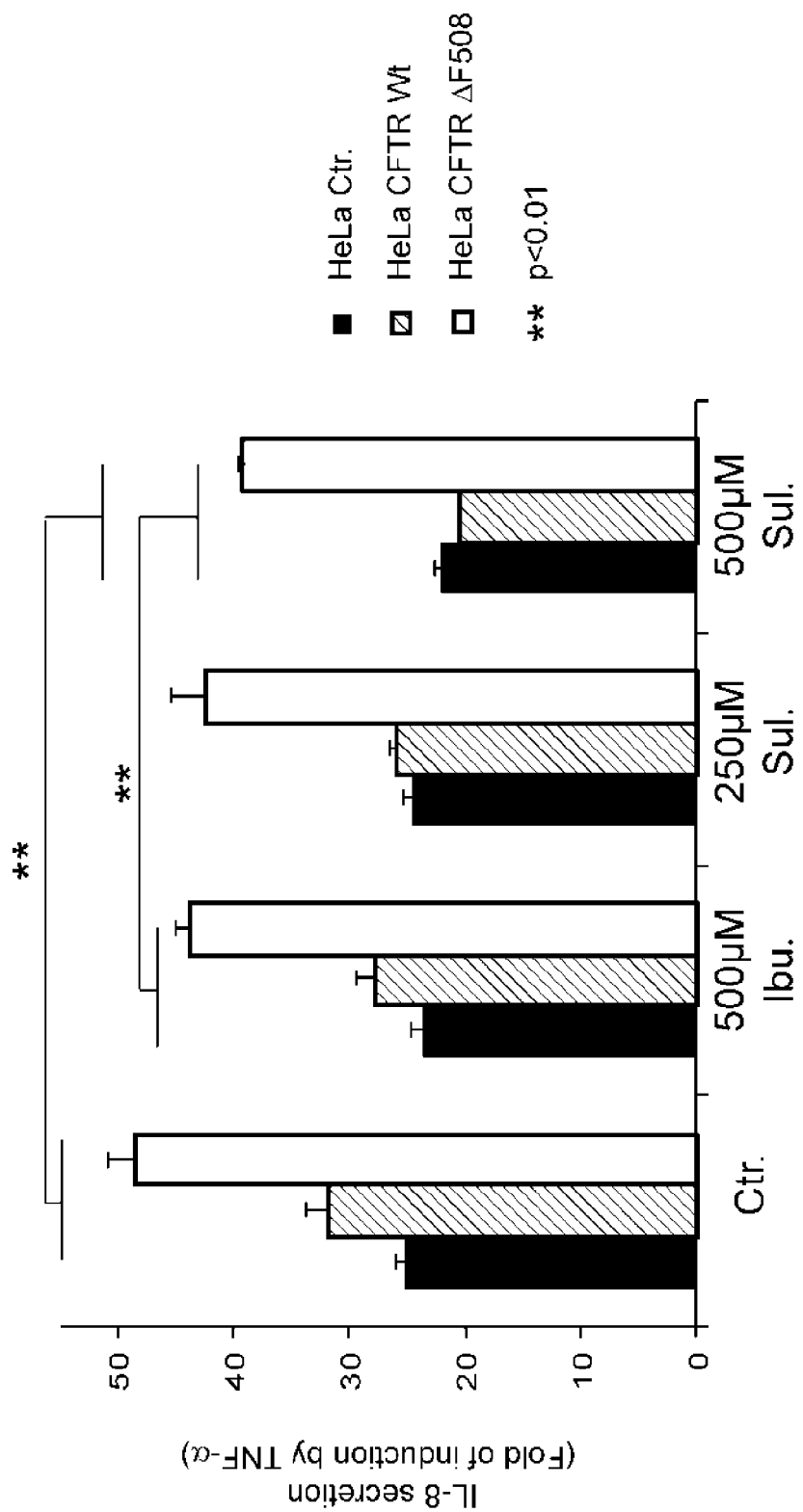

In this study, the inventors investigated the consequence of sulindac on various actors needed to be targeted in cystic fibrosis. The inventors therefore examined its effect on activation of inflammation induced by TNFα through studies of NF-κB activity, IL-8 expression and CFTR activity. The inventors have first shown that sulindac inhibits transcriptional activity of NF-κB similar to ibuprofen. This inhibitory effect was observed in bronchial epithelial cells BEAS-2B and in HeLa cells stably transfected with wild-type (wt) or deltaF508-CFTR (heterologous models) (FIGS. 1 A and B). The inventors then studied its effects on IL-8 mRNA level and secretion. Indeed, IL-8 is a transcriptional target of NF-κB and a marker of inflammation in bronchoalveolar fluid of CF patients. By contrast with ibuprofen, the inventors showed that sulindac decreased IL-8 transcription in bronchial epithelial cells and in heterologous models (FIGS. 2 A and B). This effect was also accompanied by a decrease of IL-8 secretion in bronchial epithelial cells Beas2B and Calu-3 and in heterologous systems (FIG. 2 C). The inventors further confirmed this effect in vivo in a mouse model of lung inflammation induced by intratracheal instillation of LPS (lipopolysaccharides) (FIG. 3 A). In bronchoalveolar fluid of mice, LPS induces a secretion of KC (keratinocyte-derived chemokine) and MIP-2 (macrophage inflammatory protein 2) two homologs of human IL-8. As already shown in vitro, the pretreatment by sulindac decreased the secretion of KC and MIP-2 (FIG. 3 B).

Recent studies hypothesized that wt-CFTR could have anti-inflammatory properties [11, 12]. Additionally, G. Lukacs' lab recently described that secretion of IL-8 was inversely proportional with wt-CFTR channel activity in primary human bronchial epithelia (Basic Science, ECFS, S6.2). To further investigate this area of research, the inventors studied the effect of sulindac and ibuprofen on CFTR expression, maturation and chloride channel activity. The inventors demonstrated that treatment with ibuprofen or sulindac induces a significant increase of mature form of CFTR in wt-CFTR HeLa cells (FIG. 4 A, Table 1). In the case of sulindac, this enhancement was also associated with a higher chloride channel activity in wt-CFTR HeLa cells (FIG. 4 B). An increase of CFTR activity was also observed in human primary nasal epithelial cells (FIG. 4 C) confirming that effects of sulindac on differentiated primary cultures. These data demonstrate that sulindac also act as a CFTR potentiator.

TABLE 1

Maturation of CFTR was expressed as ratio of mature CFTR to total CFTR (band B + band C) in HeLa Wt. Effects of treatment were expressed in percent of diluent.

| | | Ratio CFTR C/C + B (%) |
|---|---|---|
| HeLa | Ctr. | 65.1 |
| CFTR WT | Ibu. 500 µM | 80.6 |
| | Sul. 250 µM | 77.7 |
| | Sul. 500 µM | 81.5 |

These data are of outstanding interest because decreased lung inflammation coupled to restoration of CFTR function are the key aims of therapies in cystic fibrosis [13].

EXAMPLE 2

Material & Methods

All reagents were purchased from Sigma (St. Louis, Mo.) unless otherwise specified. Sulindac were prepared as stocks in DMSO (100 mM) and stored at −20° C. DMSO was used as a diluent control in these experiments.

Cell Culture and Treatments

The inventors used for these studies HeLa cells lines. Cells were grown at 37° C. in a 5% $CO_2$ incubator in DMEM with Glutamax (Invitrogen) and 10% fetal bovine serum (SVF). For the treatment, drugs were added in DMEM 1% SVF in order to reduce drug aggregation with the proteins contained in SVF.

Plasmid Constructs and Transient Transfection

To assay the transcriptional activity of AP-1, pAP1Luc, a *luciferase* reporter plasmid containing five sequential AP-1 binding sites upstream of a minimum promoter element, was used. Transcriptional activity of PPAR was evaluated with reporter constructs with three sequential PPRE consensus sequences, binding PPAR factors. Transient transfection were realized as described before. To normalize transfection efficiency, a *renilla luciferase* reporter construct (pRL-TK, Promega) was co-transfected with each of the firefly *luciferase* constructs. To induced AP-1 activity, cells were exposed to TNFα (10 ng/mL) for 1 hour. Cells were pre- and treated with sulindac, ibuprofen or vehicule control one hour before and four hours after this induction. For PPAR activity, cells were treated with pharmacological drugs for 24 hours.

*Luciferase* Assay

*Luciferase* assay was realized as described before.

Results In this study, the inventors investigated the effect of sulindac on two other therapeutic targets: AP-1 and PPARγ whose activity is respectively increased and decreased in cystic fibrosis. The inventors have examined the effect of sulindac on the transcriptional activity of AP-1 induced by TNF in HeLa cells and showed that sulindac causes a decrease in the induction (FIG. 5). The inventors then showed that sulindac could induce an increase in the transcriptional activity of PPAR in HeLa cells (FIG. 6). Sulindac has positive effects on various factors disrupted in cystic fibrosis.

EXAMPLE 3

Material & Methods

All reagents were purchased from Sigma (St. Louis, Mo.) unless otherwise specified. Sulindac and sulindac sulfone were prepared as stocks in DMSO (100 mM) and stored at −20° C. DMSO was used as a diluent control in these experiments.

Cell Culture and Treatments

The inventors used for these studies a heterologous model of stable HeLa that as previously described. Cells were grown at 37° C. in a 5% $CO_2$ incubator in DMEM with Glutamax (Invitrogen) and 10% fetal bovine serum (SVF). For the treatment, drugs were added in DMEM 1% SVF in order to reduce drug aggregation with the proteins contained in SVF.

Nuclear and Cytosolic Extraction and Western Blot

Nuclear and cytosolic fraction was obtained by differential centrifugation. Briefly, cells were lyses in buffer C (10 mM Hepes, 60 mM KCl, 1 mM EDTA, 7.8% NP40, 100 mM DTT, pH 7.6). After centrifugation, nucleus pellet were lyses in buffer N (27 mM Tris, 566 mM NaCl, 2 mM MgCl2, 1.3 mM EDTA, pH 8). Aliquots of fraction (30 µg protein) were separated by SDS-PAGE and transferred on PVDF membrane. The western blots were probed with mouse monoclonal antibodies specific for IκB or p65 (Santa-Cruz) 2 h at room temperature. After 1 hour of incubation with HRP anti-mouse antibodies, Chemioluminescence were revealed by ECL (GE Healthcare, Life Science) with Gene GNOME camera (Syngene Bio Imaging).

*Luciferase* Assay

The transcriptional activity of NF-κB and IL-8 promoter was measured as described before. Inflammation was induced by TNFα (10 ng/mL) for 1 hour. Cells were pre- and treated with sulindac, sulindac sulfone or vehicule control one hour before and four hours after this induction.

Results

In this study, the inventors explored the mechanism of anti-NF-κB effects of sulindac. The inventors have shown that sulindac did not affect the degradation of IκB induced by TNFα (FIG. 7A) and that did not prevent the nuclear translocation of NF-κB (FIG. 7B). At the NF-κB pathway, sulindac effect is downstream of the nuclear translocation of NF-κB.

The inventors have also demonstrated that sulindac sulfone (metabolite of sulindac described to be inactif on COX) inhibits the transcriptional activity of NF-κB (FIG. 8A) and also the IL-8 promoter (FIG. 8B). Therefore, this activity of sulindac is independent of anti-COX activity.

The therapeutic effects of sulindac are not due to the main target of NSAIDs (COX) and sulindac COX inactive derivatives may be effective or more effective that sulindac in cystic fibrosis.

REFERENCES

Throughout this application, various references describe the state of the art to which this invention pertains. The disclosures of these references are hereby incorporated by reference into the present disclosure.

[1] Jacquot, J., Tabary, O., Le Rouzic, P. and Clement, A. (2008). Airway epithelial cell inflammatory signalling in cystic fibrosis. Int J Biochem Cell Biol 40, 1703-15.

[2] Konstan, M. W. (2008). Ibuprofen therapy for cystic fibrosis lung disease: revisited. Curr Opin Pulm Med 14, 567-73.

[3] Konstan, M. W., Byard, P. J., Hoppel, C. L. and Davis, P. B. (1995). Effect of high-dose ibuprofen in patients with cystic fibrosis. N Engl J Med 332, 848-54.

[4] Lands, L. C., Milner, R., Cantin, A. M., Manson, D. and Corey, M. (2007). High-dose ibuprofen in cystic fibrosis: Canadian safety and effectiveness trial. J Pediatr 151, 249-54.

[5] Dauletbaev, N., Lam, J., Eklove, D., Iskandar, M. and Lands, L. C. (2010). Ibuprofen modulates NF-κB activity

[6] Thompson, H. J., Jiang, C., Lu, J., Mehta, R. G., Piazza, G. A., Paranka, N. S., Pamukcu, R. and Ahnen, D. J. (1997). Sulfone metabolite of sulindac inhibits mammary carcinogenesis. Cancer Res 57, 267-71.

[7] Piazza, G. A., Rahm, A. K., Finn, T. S., Fryer, B. H., Li, H., Stoumen, A. L., Pamukcu, R. and Ahnen, D. J. (1997). Apoptosis primarily accounts for the growth-inhibitory properties of sulindac metabolites and involves a mechanism that is independent of cyclooxygenase inhibition, cell cycle arrest, and p53 induction. Cancer Res 57, 2452-9.

[8] Williams, C. S., Watson, A. J., Sheng, H., Helou, R., Shao, J. and DuBois, R. N. (2000). Celecoxib prevents tumor growth in vivo without toxicity to normal gut: lack of correlation between in vitro and in vivo models. Cancer Res 60, 6045-51.

[9] Goluboff, E. T. et al. (1999). Exisulind (sulindac sulfone) suppresses growth of human prostate cancer in a nude mouse xenograft model by increasing apoptosis. Urology 53, 440-5.

[10] Tegeder, I., Pfeilschifter, J. and Geisslinger, G. (2001). Cyclooxygenase-independent actions of cyclooxygenase inhibitors. FASEB J 15, 2057-72.

[11] Vij, N., Mazur, S. and Zeitlin, P. L. (2009). CFTR is a negative regulator of NFkappaB mediated innate immune response. PLoS One 4, e4664.

[12] Hunter, M. J., Trehame, K. J., Winter, A. K., Cassidy, D. M., Land, S. and Mehta, A. (2010). Expression of wildtype CFTR suppresses N F-kappaB-driven inflammatory signalling. PLoS One 5, el 1598.

[13] Ashlock, M. A. et al. (2009). A pipeline of therapies for cystic fibrosis. Semin Respir Crit Care Med 30, 611-26.

[14] Tanguy, G., Drevillon, L., Arous, N., Hasnain, A., Hinzpeter, A., Fritsch, J., Goossens, M. and Fanen, P. (2008). CSN5 binds to misfolded CFTR and promotes its degradation. Biochim Biophys Acta 1783, 1189-99.

[15] Edwards, M. R., Mukaida, N., Johnson, M. and Johnston, S. L. (2005). IL-1beta induces IL-8 in bronchial cells via NF-kappaB and NF-IL6 transcription factors and can be suppressed by glucocorticoids. Pulm Pharmacol Ther 18, 337-45.

[16] Cheng K W, Wong C C, Alston N, Mackenzie G G, Huang L, Ouyang N, Xie G, Wiedmann T, Rigas B. (2005) Aerosol administration of phospho-sulindac inhibits lung tumorigenesis. Mol Cancer Ther. 2013 May 3.

[17] Zhou H, Liu W, Su Y, Wei Z, Liu J, Kolluri S K, Wu H, Cao Y, Chen J, Wu Y, Yan T, Cao X, Gao W, Molotkov A, Jiang F, Li W G, Lin B, Zhang H P, Yu J, Luo S P, Zeng J Z, Duester G, Huang P Q, Zhang X K. NSAID sulindac and its analog bind RXRalpha and inhibit RXRalpha-dependent AKT signaling. Cancer Cell. 2010 Jun. 15; 17(6):560-73. doi: 10.1016/j.ccr.2010.04.023.

The invention claimed is:

1. A method for treating cystic fibrosis in a subject in need thereof, consisting of administering a compound selected from the group consisting of sulindac, sulindac sulfide, sulindac sulfone, or phospho-sulindac.

2. A method for treating cystic in a subject in need thereof, consisting of administering to said subject sulindac.

* * * * *